United States Patent
Baltay et al.

(10) Patent No.: US 12,207,936 B2
(45) Date of Patent: *Jan. 28, 2025

(54) EYE SENSOR, SYSTEM AND METHOD

(71) Applicant: BRAINSTEM BIOMETRICS, INC., Lincoln, MA (US)

(72) Inventors: Michael Baltay, Lincoln, MA (US); Bruce Rasmussen, Acton, MA (US); Yahya Shehabi, Maroubra (AU); Ciaran Bolger, Malahide (IE); Martin Acquadro, Wellesley, MA (US); Clark B. Foster, Mission Viejo, CA (US)

(73) Assignee: BRAINSTEM BIOMETRICS, INC., Lincoln, MA (US)

( * ) Notice: Subject to any disclaimer, the term of this patent is extended or adjusted under 35 U.S.C. 154(b) by 809 days.

This patent is subject to a terminal disclaimer.

(21) Appl. No.: 17/146,152

(22) Filed: Jan. 11, 2021

(65) Prior Publication Data
US 2021/0236051 A1 Aug. 5, 2021

Related U.S. Application Data

(63) Continuation of application No. 15/373,434, filed on Dec. 8, 2016, now Pat. No. 10,888,268.

(51) Int. Cl.
*A61B 5/00* (2006.01)
*A61B 3/00* (2006.01)
(Continued)

(52) U.S. Cl.
CPC .......... *A61B 5/4821* (2013.01); *A61B 3/0025* (2013.01); *A61B 3/0041* (2013.01);
(Continued)

(58) Field of Classification Search
None
See application file for complete search history.

(56) References Cited

U.S. PATENT DOCUMENTS

| 3,948,248 A | 4/1976 | Zuckerman et al. |
| 4,836,219 A * | 6/1989 | Hobson ................ A61B 5/1103 |
| | | 600/595 |

(Continued)

FOREIGN PATENT DOCUMENTS

| CN | 103780143 | 5/2014 |
| JP | H05168599 A * | 7/1993 |
| WO | WO-2012/136431 A1 | 10/2012 |

OTHER PUBLICATIONS

English machine translation of JP H05168599 A, Clarivate Analytics, pp. 1-4, printed on Nov. 2, 2023. (Year: 2023).*

(Continued)

*Primary Examiner* — Matthew Kremer
(74) *Attorney, Agent, or Firm* — Hathaway P. Russell; Stephen J. Kenny; Foley Hoag LLP

(57) ABSTRACT

An eye sensor, system and method for measuring fixational eye movements of an individual's eyeball (e.g., ocular microtremors and microsaccades) to provide a variable voltage biosignal for measuring the individual's brain stem activity. The eye sensor comprises a sensor mounted on the individual's closed or opened eyelid so as to be deflected by the fixational eye movements of the eyeball. A shielded flexible ribbon assembly supplies the biosignal generated by the sensor to an amplifier located on the individual's skin where the biosignal is amplified. The amplifier is interconnected with a signal processor and a display by which graphical and numerical representations of the biosignal are made accessible to an anesthesiologist, intensivist or clinician. A method for analyzing the biosignal to determine the brainstem activity of a patient.

19 Claims, 22 Drawing Sheets

(51) Int. Cl.
*A61B 3/113* (2006.01)
*A61B 5/16* (2006.01)
*A61B 5/18* (2006.01)

(52) U.S. Cl.
CPC .............. *A61B 3/113* (2013.01); *A61B 5/002* (2013.01); *A61B 5/163* (2017.08); *A61B 5/6833* (2013.01); *A61B 5/18* (2013.01); *A61B 5/7203* (2013.01); *A61B 5/7257* (2013.01); *A61B 2562/0247* (2013.01); *A61B 2562/043* (2013.01)

(56) References Cited

U.S. PATENT DOCUMENTS

| | | | |
|---|---|---|---|
| 4,863,259 A | 9/1989 | Schneider et al. | |
| 5,566,067 A * | 10/1996 | Hobson | G08B 21/06 |
| | | | 702/75 |
| 7,011,410 B2 * | 3/2006 | Bolger | A61B 5/725 |
| | | | 606/4 |
| 7,959,578 B2 | 6/2011 | Lonky | |
| 8,025,404 B2 | 9/2011 | Bolger et al. | |
| 8,944,602 B2 | 2/2015 | Eberl et al. | |
| 9,788,760 B2 | 10/2017 | Baltay et al. | |
| 10,791,926 B2 | 10/2020 | Macknik et al. | |
| 10,856,774 B2 | 12/2020 | Baltay et al. | |
| 10,888,268 B2 * | 1/2021 | Baltay | A61B 3/0025 |
| 2002/0085174 A1 | 7/2002 | Bolger et al. | |
| 2006/0082727 A1 | 4/2006 | Bolger et al. | |
| 2009/0198148 A1 | 8/2009 | Lonky | |
| 2010/0191156 A1 * | 7/2010 | Sakamoto | A61B 5/165 |
| | | | 600/595 |
| 2014/0180161 A1 | 6/2014 | Bolger et al. | |
| 2015/0257699 A1 * | 9/2015 | Bjerrum | A61B 3/113 |
| | | | 340/575 |
| 2018/0116558 A1 | 5/2018 | Baltay et al. | |
| 2018/0136492 A1 | 5/2018 | An et al. | |
| 2021/0113115 A1 | 4/2021 | Baltay et al. | |

OTHER PUBLICATIONS

Al-Kalbani et al., "An automated ocular microtremor feature extraction using the gabor thresholding technique," 2007 Annual International Conference of the IEEE Engineering in Medicine and Biology Society: [EMBC '07], 2851-2854 (2007).

Extended European Search Report for EP Application No. 16873870.6 mailed Jul. 16, 2019.

International Search Report and Written Opinion for International Application No. PCT/US2016/065679 dated Feb. 17, 2017.

Sheahan et al., "Ocular microtremor measurement system: Design and performance," Medical and Biological Engineering and Computing, 31(3):205-212 (1993).

English Translation of Chinese Patent No. CN-103780143-A (2014).

* cited by examiner

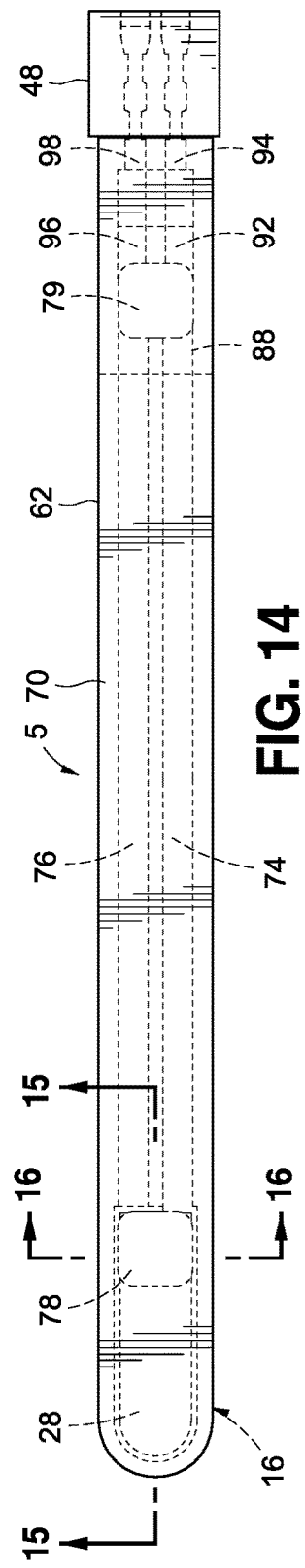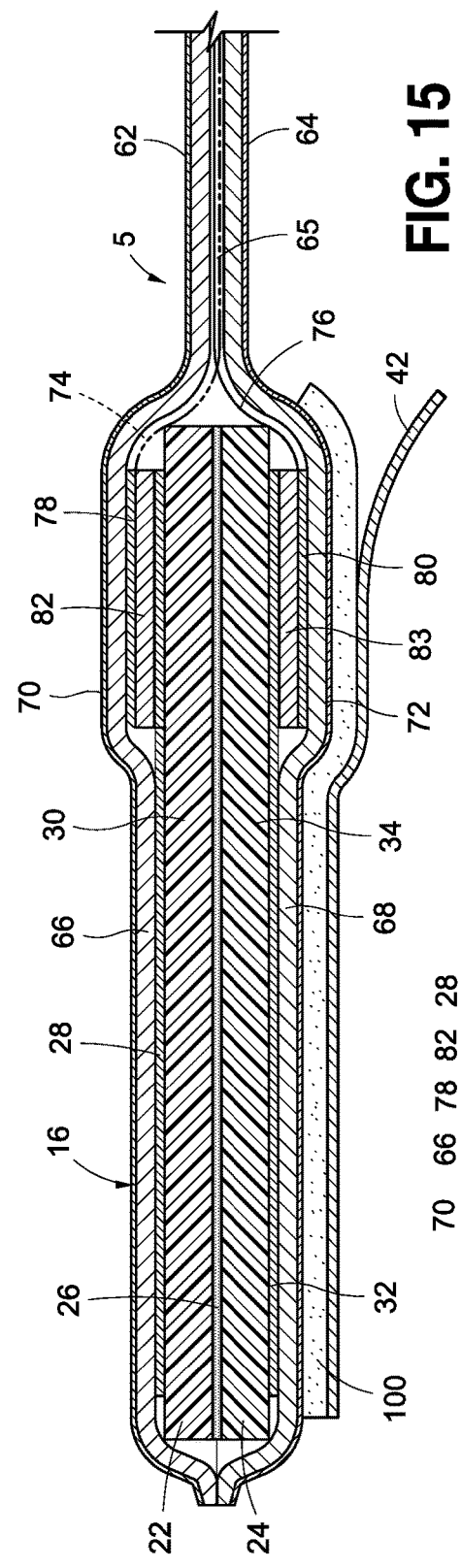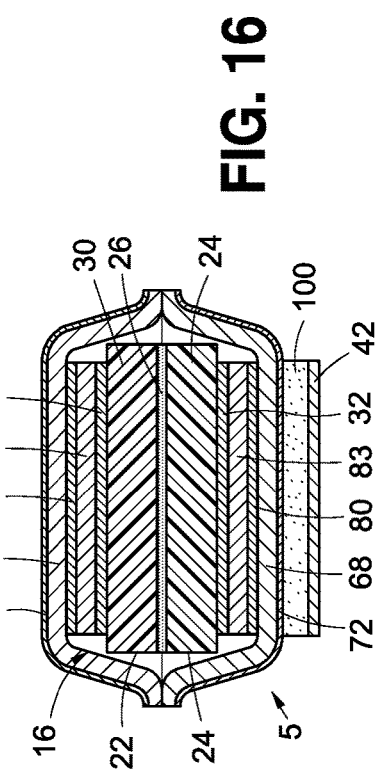

EYE SENSOR, SYSTEM AND METHOD

This disclosure is a Continuation application of and claims the benefit under 35 U.S.C. 121 of U.S. application Ser. No. 15/373,434 filed Dec. 8, 2016.

BACKGROUND OF THE INVENTION

Field of the Invention

This invention relates to an eye sensor, system and method which displays graphical and numerical representations of one or more of the fixation eye movements of a patient's eyeball (e.g., the cornea/sclera) to provide a monitor (e.g., an anesthesiologist, intensivist or clinician) with an indication of the patient's brain stem activity or altered brainstem state including his level of sedation, consciousness and responsiveness. This can be used prior to, during and after a medical or clinical procedure, such as, for example, when the patient is anesthetized during an operation. A sensor of the eye sensor is thin and compliant and capable of conforming to the shape of the patient's closed eyelid or being located in the tissue folds of the patient's open eyelid at which to be responsive to the fixational eye movements of the patient's eyeball.

Background Art

During the performance and treatment of many medical procedures and conditions, anesthesia is administered so that a patient is sedated and rendered unconscious. In some cases, the patient may be over-sedated throughout an operation which could permanently impact his neural ability and possibly cause brain stem death. In other situations, the patient may be under sedated and immobilized without having the ability to alert medical personnel to a level of consciousness which subjects the patient to pain. In still other cases, over-sedation of a patient may prolong the duration of mechanical ventilation, and under-sedation can result in the patient being subjected to unintended extubation.

For a long time, a primary source of information available to a clinician concerning the depth of anesthesia or sedation was limited to the patient's somatic and autonomic response to physical and/or verbal stimuli. These responses are known to be susceptible to being altered and influenced by neuromuscular blocking drugs, drugs affecting the autonomic nervous system, and the inconsistency of the stimuli. Thus, the presence or absence of these responses does not always accurately correlate with conscious awareness and, therefore, can be poor indicators of the depth of the patient's unconscious state.

Microsaccades (MS) (not to be confused with their larger counterpart, saccadic movements) consist mostly of single wave actions, erratic with bursts and periods of high activity accompanied by periods of no activity and are typically measured in terms of time between intervals, on the order of one burst per second. Therefore the frequency of microsaccades tends to be less reported as useful, and more often the direction, presence or lack of, peak speed or acceleration and amplitude as measures of various phenomenon. Ocular microtremors (OMT) on the other hand is always tremoring continuously except at death and other rare conditions. OMT tends to be measured in frequency and is used as an indicator of overall activity levels awareness and arousal with trend analysis, ranging from near zero to 100 Hz, in part because prior measurement techniques are prone to variation when measuring such small amplitudes. OMT amplitude ranges are much narrower than microsaccadic ranges both in absolute and, especially, relative terms. Historically dominant high-frequency counts are the primary units of measure used for trend wise continuous measurements and not to measure reaction power or response to a stimulus.

MS achieve the highest acceleration and speeds of all eye motions, aptly named "flicks", and these motions are known to act rapidly rising quickly in an exponential fashion, and similarly, to disappear or drop below measurement levels equally rapidly. Measures of microsaccades consider OMT to be of insignificant value for visual experiments, outside the range of interest and typically below the level of detection of microsaccadic measurement systems. Until the present disclosure conventional wisdom taught that microsaccade events microsaccades are either "present" or not "present" and taught to be of primary visual purpose and origin, and only on occasion suggested for use in the measurement of conscious-sedated patients limited to awake patient conditions, again where open eye visual stimuli and action can be detected.

Sensors are known in the prior art which are responsive to microsaccades (MS) and/or Ocular Micro Tremor (OMT) of an individual undergoing testing. Sensors are also known which are adhesively bonded over the patient's closed eyelid to sense large voluntary (e.g. 20-degree gross excursion) motions of the patient's eyeball. However, the known sensors are relatively large, such that they are limited to being used during surgery when the eyes of the individual being tested are fully closed and taped shut. Because small micro eye movements have an amplitude of about 500 nanometers, sensor these motions are susceptible to being masked or altered by external electrical and electromagnetic interference as well as physical forces and biological artifacts. Therefore, what is needed now is an improved sensor and a sensor system that are capable of generating a clean biosignal that accurately reflects the fixational eye movements (e.g. MS & OMT) of the patient's eyeball (e.g., having an amplitude of an eyeball arc length excursion between 0.1 and 400 micrometers) by reducing unwanted artifacts, both seismic and electrical, and by amplifying the information content of the biosignal without also amplifying the undesirable background noise.

The eye sensor should be capable of measuring a range and sensitivity adequate to capture the full range of motions known for the fixational movements. As such the eye sensor should be able to measure movements of the eyeball perimeter of arc motion lengths between 0.1 microns and 400 microns, representing the smallest recorded OMT excursion at the lower limit and the largest microsaccadic excursion on the upper limit. Accordingly, the widest reported range of motion of OMT is from 0.1-2.5 and more commonly 0.5-1.5 with a reported average excursion of approximately 1 micrometers arc length. Accordingly, the widest reported range of motion of MS is from 3-403 and more commonly 16-151 with a reported average excursion of approximately 45 microns micrometers arc length. For frequency the OMT component ranges from zero on death and other rare conditions up to as high as 200 hertz, commonly in the range of 20-90, with a mean value of approximately 84 hertz in healthy awake adults. The MS component ranges from less than one hertz up to 25 hertz, and is commonly reported in the 1-13 hertz range not including natural resonances and additional burst periods. The reported MS values are taken predominantly from awake patient records, and the available information available about the characteristics of MS in unconscious patients or those under depressed brainstem conditions is spare to none.

Unwanted artifacts can also be introduced by the connection from the sensor to the other items of the system. Given that the movements being measured are so small, any movement of the sensor can register. Thus there must be considerable attention to isolating the sensor from movement transmitted by the signal transmission means. Additionally, once the sensor registers some movement of the eye and produces a signal, that signal (e.g. electrical) must be protected from interference present in the testing environment, and great care must be provided to maintain the integrity of the signal.

It has been found that attaching some conventional ocular microtremor sensor to a patient's eyelid may result in a focused pressure being applied to the eyelid which creates a depression in the patient's eyeball. The sometimes intrusive nature of the conventional sensor applying a concentrated pressure to the patient's eyeball can, over time, cause patient discomfort. In this and other cases, a conventional sensor may require additional intervention and controls to ensure its proper position placement in order to be capable of responding to the patient's eye motions. What is even more, the patient may resist wearing the conventional sensor to avoid the discomfort caused by the pressure being applied to his eyeball.

Moreover, to maximize its application, the improved sensor should be of low cost, able to avoid contamination and compact so as to be capable of being attached directly to the individual's closed eyelid or in the tissue folds thereof at which to be responsive to the fixational eye movements while the patient is wholly or partly asleep or awake and while his eyelid is fully closed, fully open or blinks between being opened and closed. In this same regard, the sensor must be sufficiently compliant so as to avoid applying uncomfortable focused pressure forces to the patient's eye and be easily attached in a convenient manner so as to be worn comfortably with the patient being substantially unaware of its presence.

SUMMARY OF THE INVENTION

In general terms, an eye sensor, system, and method are disclosed having an application for providing a monitor (e.g. anesthesiologist, intensivist, clinician, or the like) with a reliable indication of a patient's level of brain stem activity or altered brainstem state including his level of sedation, responsiveness and consciousness. At times prior to, during and following a medical procedure or evaluation such as in the case of anesthesia administered to the patient during an operation. The eye sensor comprises an electrically active sensing element such as, for example, a sensor of a detector that can be attached directly over the patient's closed eyelid or in the tissue folds of his opened eyelid so as to be responsive to the fixational eye movements of the patient's eyeball (e.g., the cornea/sclera) having an amplitude of an eyeball arc length excursion between 0.1 and 400 micrometers. The eye sensor also comprises a shielded flexible ribbon assembly by which an alternating voltage biosignal generated by the detector is supplied to a shielded eye signal amplifier. The amplified output of the eye signal amplifier of the eye sensor is provided first to a signal processor and then to a visual display which provides graphical and numerical representations of the biosignal and the patient's brain stem activity and level of consciousness.

Importantly through a series of studies and experiments, it has been found that microsaccades are an excellent measure of brainstem response, especially at low levels previously unstudied and when combined together with OMT signals provide a powerful new means to diagnose brainstem states and patient conditions that until now were not feasibly possible. It has become known to the applicant that eye motions of the characteristics of microsaccades and distinctly uncharacteristic of OMT are present at all levels of the continuum from deeply anesthetized to wide awake, that on average their frequency (mean, intersaccadic interval, rate, and velocity) and burst pattern remains relatively steady across the continuum. The amplitude, power, and energy of the microsaccades appear to vary in dramatic fashion, perhaps logarithmically or exponentially. It is also discovered that microsaccades tend to burst forcefully, in nearly square wave fashion upon rapid increases of arousal, reactions to stimuli and other awakening phenomenon and events. The strength and power of the microsaccades appear to be proportional to the responsiveness of the brainstem, especially at lower levels of the continuum; or upon light responses to mild stimuli; or upon tempered responses or responses to more noxious stimuli (e.g., by drugs or other brainstem function attenuation mechanisms such as sleep). Conversely, we observe that the amplitude, power or energy of microsaccadic eye movements decreases dramatically upon cessation of stimulus. The power of microsaccade movements also drops upon the loss of consciousness such as induced by sleep or drug agents. However, the transition although clearly distinct and relatively abrupt, is not so sharply defined as that for awakening. At higher levels of arousal, microsaccadic responses appear proportional to the strength of stimulus and the brainstem's attenuation level. However, proportional changes seem much less dramatic. This phenomenon observed by the applicant at awake levels helps to explain current teachings that it is the presence or lack thereof, the direction, density of focus, short-term firing rate peak velocity of single waves that is clinically relevant, again especially on awake subjects in response to visual stimuli.

It is disclosed further that certain combinations of these fixational eye movement parameters such as those of microsaccade responses or reactions to stimuli and the steady trending patterns of their OMT patterns can be recognized as signatures to diagnose and distinguish between various states that were undistinguishable by measuring either of the parameters alone.

It has been found that contemporaneously measuring two or more types of fixational eye movements (e.g. MS and OMT) can provide better insight into the state of the patient. By monitoring these two or more types of fixational eye movement, unique patterns can be found and compared to predetermined values and suggest, and/or automatically take, an action in response to the condition. The use of two or more fixational eye movements enables clinicians to better diagnose a patient's condition in the circumstance where differing underlying conditions present similarly and are previously indistinguishable using conventional instruments single parameter measures and methods available prior to the present invention.

While the invention is described in terms of MS and OMT movements, it is hypothesized that drift and other fixational movements, when monitored will provide data representative of brainstem activity. What has been discovered is by monitoring at least two fixational eye movements, previously believed by the prior art to be only of independent value, actually better diagnose the state of brainstem than the individual data points.

For example, the use of two or more types of fixational eye movement provides valid objective data for clinicians to distinguish between:
- transient increases in physical and brain activity resulting as a response to stimulus versus fundamental shifts in the level of sedation or anesthesia;
- sleep state depression of activity versus drug-induced depression of activity;
- conscious awareness versus unconsciousness lack of awareness when paralyzed by drugs, absent usual physical activity indicators;
- mild versus moderate levels of sedation or other subtle grades, which often present similarly; and
- gradations of "non-responsiveness" or continuum of brain state activity present below the physically observable cutoff point. These conditions are not clearly distinguished by OMT frequency measurements alone. While the OMT frequency can indicate these states, often times similar OMT frequency readings are present for multiple states, as is the case with most singular sets of data. Likewise, microsaccadic motions, reactivity patterns, and bursts, while excellent indicators of strength and speed of response, are less valuable in evaluating general trends and gradual changes. During a given length of time of known similar underlying drug dose and effect on the brainstem, one might observe periods of prevalent strong microsaccadic events associated with multiple stimuli and immediate adjacent periods of the opposite. Without additional information, observers of microsaccadic reactivity might draw incorrect conclusions, possibly leading to improper administration of lethal drugs.

Some embodiments comprise a sensor system designed to both capture the full range of both MS and OMT motions, to be of appropriate sensitivity and noise reduction to measure both signals, and to be able to do so under the full range of behavioral conditions of the eye being open or closed and across the gamut of subject being fully awake and aware to deeply anesthetized under medical coma conditions.

Some embodiments comprise a system to process the MS and OMT movements and determine the frequency of the OMT and a combined data; wherein the combined data comprises combined microsaccades (MS) amplitude and OMT amplitude, combined MS and OMT power, combined MS and OMT reactivity, or a combination thereof.

In some embodiments, the sensor of the eye sensor comprises a piezoelectric element. One embodiment incorporates a single thick piezo layer in the range of 10-60 um thick which is laminated together with an adjacent structural layer of approximately equal thickness as the piezo layer so as to maximize stress and strain and sensitivity. In some embodiments, piezoelectric element comprises upper and lower thin film forming piezoelectric layers that are joined one above the other in an opposing bimorph fashion by an intermediate bonding agent. In some embodiments, the outside of each of the upper and lower piezoelectric layers has an electrically conductive surface electrodes directly disposed upon the piezo layer to collect the signal created by movement. The sensor of the detector is able to generate the alternating voltage biosignal between the outside conductive surfaces as the upper and lower piezoelectric layers thereof are deflected in response to fixational eye movements of the patient's eyeball. To increase its sensitivity, enable proper transduction reliably without the need for additional measures, enable use during both open and closed eye conditions, and to reduce the discomfort of the wearer, the sensor is attached to the patient's eyelid so as to conform to the shape thereof. Additionally, the sensing element is covered with outer layers of conductive shielding, which are insulated from the conducting electrodes that are disposed of inside.

While the present embodiments disclose the use of a conforming piezoelectric sensor technology, it is (may be) suitable to employ any number of alternative technologies.

An embodiment of the flexible ribbon cable, which extends between the sensor and the amplifier, comprises a non-conductive film strip. The flexible ribbon assembly is shielded from external electrical and electromagnetic interference by electrically conductive shielding layers that lie on the outside of the upper strip surface and to the outside of the lower non-conductive insulating layers. One or more electrically conductive traces runs longitudinally along the inside of the ribbon in electrical isolation from one another and the electrically conductive shielding coatings. In some embodiments, the piezoelectric element is sandwiched between the opposing upper and lower non-conductive strips at the proximal end of the flexible ribbon assembly so that the electrically conductive outside surfaces of the sensing element lie in electrical contact with electrical terminals formed at first ends of the conductive traces that run along the upper and lower strips. A flexible circuit board is located, in some embodiments sandwiched, between the opposing upper and lower non-conductive strips at the terminal end of the flexible ribbon assembly so as to lie in electrical contact with electrical terminals formed at the opposite ends of the conductive traces. The flexible circuit board at the terminal end of the flexible ribbon assembly is coupled to an electrical connector block that is located in the interior of the eye signal amplifier. Accordingly, the alternating voltage biosignal generated by a piezoelectric element of the detector is supplied to the eye signal amplifier by way of the electrically conductive traces that run along the upper and lower non-conductive strips of the flexible ribbon assembly.

The amplifier of the eye sensor to which the alternating voltage biosignal is supplied from the detector, and the shielded flexible ribbon assembly comprises an electrically conductive housing that shields the biosignal from external electrical and electromagnetic interference. In some embodiments, the amplifier housing is attached by an electrically conductive adhesive patch to the patient skin. A printed circuit board which lies at the bottom of and within the amplifier housing is coupled to a grounding electrode that extends through the housing to be held against the patient's skin. The electrically conductive traces, which run along the flexible ribbon assembly and carry the fixational eye movement biosignal from the sensing element, are connected to the printed circuit board for amplification by means of the aforementioned connector block located within the housing of the eye signal amplifier. First and second electrically conductive mesh pillows can lie inside the amplifier housing so as to contact respective ones of the electrically conductive shielding that lie on the outside of the upper and lower non-conductive strips of the ribbon assembly. The mesh pillows lie in circuit paths by which the shielding coatings of the ribbon assembly are connected to each other and to electrical ground at the patient's skin by way of the grounding electrode through the bottom of the amplifier housing. The output of the eye signal amplifier is supplied from the printed circuit board thereof to the signal processor by way of either a shielded cable from the amplifier housing or a wireless transmitter that is located within the amplifier housing and communicates with a remote transceiver of the signal processor.

There are many embodiments disclosed herein. Some of the embodiments are mentioned below.

A method comprising: obtaining output signals from an eye sensor configured to produce the output signals that are indicative of eye movement; and deriving a frequency and combined data from the output signals; wherein the frequency is of OMT frequency, and the combined data comprises combined MS amplitude and OMT amplitude, combined MS and OMT power, combined MS and OMT reactivity, or a combination thereof. The eye sensor can comprise a detector, and the detector comprises a sensor; and the sensor is located on an eyelid. The eye sensor can comprise a detector and an amplifier; the detector comprises a sensor; the amplifier is grounded to skin; and the sensor is located on an eyelid. There can be amplifying the output signals to render amplified output signals, and the deriving the frequency and the combined data comprises processing the amplified output to isolate the frequency and the combined data. The obtaining output signals comprises can be producing a voltage in response to an eye movement by a piezoelectric element; transmitting a current along an electrical connection. There can be amplifying the output signals to render amplified output signals; wherein the obtaining output signals comprises: producing a voltage in response to an eye movement by a piezoelectric element, wherein the eye sensor comprises the piezoelectric element; transmitting a current along an electrical connection. The electrical connection can comprise a shielded ribbon. The eye sensor can comprise a sensor that is located in a tissue fold or an open eyelid. The deriving the frequency and combined data can comprise: processing the output signals by a processor; wherein the processing output signals comprises: isolating the eye movement attributed to OMT and MS, determining the frequency of the OMT, and determining the combined amplitude of OMT and the MS, the combined power of the OMT and the MS, the reactivity, or a combination thereof. There can also be displaying results, wherein the displaying results comprises presenting a representation of the frequency and the combined amplitude of OMT and the MS, the combined power of the OMT and the MS, the reactivity, or a combination thereof. The presenting a representation can comprise showing a frequency representation and a combined data representation, and the frequency representation is shown at substantially contemporaneous as the combined data representation. There can also be compiling the frequency and the combined data to arrive as reference number; and displaying the reference number. There can also be comparing the frequency, the combined data, or both the frequency and the combined data to pre-known values, pre-known patterns, or both pre-known values and pre-set patterns. There can also be displaying an alert or suggested action based upon the comparing.

A method can comprise: obtaining output signals from an eye sensor configured to produce the output signals that are indicative of eye movement; shielding the output signals; amplifying the output signals to obtain amplified output signals; processing the amplified output signals to determine a frequency and an combined data; wherein the frequency is of ocular microtremors (OMT) frequency and the combined data comprises combined microsaccades (MS) amplitude and OMT amplitude, combined MS and OMT power, combined MS and OMT reactivity, or a combination thereof; and displaying the frequency and the combined data.

A method can comprise obtaining output signals from an eye sensor configured to produce the output signals that are indicative of eye movement; shielding the output signals; amplifying the output signals to obtain amplified output signals; processing the amplified output signals to determine a frequency and a combined data; wherein the frequency is ocular microtremors (OMT) frequency and the combined data comprises combined microsaccades (MS) amplitude and OMT amplitude, combined MS and OMT power, combined MS and OMT reactivity, or a combination thereof; and comparing the frequency, the combined data, or both the frequency and the combined data to pre-known values, pre-known patterns, or both pre-known values and pre-set patterns. There can also be an alert or suggested action based upon the comparing.

A method can comprise obtaining output signals from an eye sensor configured to produce the output signals that are indicative of eye movement of an unconscious mammal; shielding the output signals; amplifying the output signals to obtain amplified output signals; processing the amplified output signals to determine a frequency and a combined data; wherein the frequency is ocular microtremors (OMT) frequency and the combined data comprises combined microsaccades (MS) amplitude and OMT amplitude, combined MS and OMT power, combined MS and OMT reactivity, or a combination thereof; and comparing the frequency, the combined data, or both the frequency and combined data to pre-known values, pre-known patterns, or both pre-known values and pre-set patterns. A method can comprise obtaining output signals from an eye sensor configured to produce the output signals that are indicative of eye movement; processing the output signals to determine a frequency and a combined data; wherein the frequency is ocular microtremors (OMT) frequency and the combined data comprises combined microsaccades (MS) amplitude and OMT amplitude, combined MS and OMT power, combined MS and OMT reactivity, or a combination thereof; and detecting an event according to the frequency, combined data or frequency and combined data; evaluating the event; and comparing the frequency, the combined data, or both the frequency and amplitude to pre-known values, pre-known patterns, or both pre-known values and pre-set patterns. The evaluating the event can comprise analyzing a fold change.

An apparatus can comprise a detector comprising: a sensor comprising: a piezoelectric element with a first surface and a second surface; a first electrically conductive surface in electrically coupled the first surface; and a second electrically conductive surface in electrically coupled to the second surface; and a ribbon, coupled to the sensor, comprising: a trace; a conductive shield; and an electrical insulator; wherein the trace is electrically coupled with first electrically conducting surface; the electrical insulator is located between first electrically conductive surface and the conductive shield; the sensor is configured to conform to a shape of an eye; and the sensor is configured to register micro-movements of an eyeball having an amplitude of an eyeball arc length excursion between 0.1 and 400 micrometers.

An apparatus can comprise: a sensor comprising: a sensing element comprising: a piezoelectric element with a first surface and a second surface; a first electrically conductive surface in direct contact with first surface; a second electrically conductive surface in direct contact with second surface; and a flexible ribbon assembly comprising a conducting trace; a conductive shield; and an electrical insulator; wherein the conductive trace is in electrical communication with first electrically conducting surface; the electrical insulator is located between first electrically conductive surface and the conductive shield; the sensor is configured to conform to a shape of an eye; and a flexural rigidity of the flexible ribbon assembly is less than or equal to $10 \times 10^{-4}$ lbs-in$^4$.

An apparatus can comprise: a sensor comprising: a sensing element comprising: a piezoelectric element with a first surface and a second surface; a first electrically conductive surface in direct contact with first surface; a second electrically conductive surface in direct contact with second surface; and a flexible ribbon assembly comprising a conducting trace; a conductive shield; and an electrical insulator; wherein the conductive trace is in electrical communication with first electrically conducting surface; the electrical insulator is located between first electrically conductive surface and the conductive shield; the sensor is configured to conform to a shape of an eye; and thickness of the ribbon assembly is less than or equal to 25 micrometers.

An apparatus can comprise: a detector comprising: a sensor comprising: a sensing element; a conductive top surface abutting the sensing element; a conductive bottom surface abutting the sensing element; a ribbon comprising: a trace; and a conductive shield; wherein the ribbon is coupled to the sensor; the trace is insulated from conductive shield; and the trace is coupled to either the conductive top surface or the conductive bottom surface.

An apparatus can comprise: a detector comprising: a sensor comprising: a sensing element; a conductive top surface abutting the sensing element; a conductive bottom surface abutting the sensing element; a ribbon comprising: a trace; and a conductive shield; wherein the ribbon is coupled to the sensor; the trace is insulated from conductive shield; and the trace is coupled to either the conductive top surface or the conductive bottom surface.

An apparatus can comprise: a detector comprising: a sensor comprising: a sensing element; a conductive top surface abutting the sensing element; a conductive bottom surface abutting the sensing element; a ribbon comprising: a trace; and a conductive shield; wherein the ribbon is coupled to the sensor; the trace is insulated from conductive shield; the trace is coupled to either the conductive top surface or the conductive bottom surface; the sensor is configured to conform to a shape of an eye; and the sensor is configured to register micro-movements of an eyeball having an amplitude between 0.1 and 400 micrometers as low of an eyeball arc length excursion.

An apparatus can comprise: a detector comprising: a sensor comprising: a sensing element; a conductive top surface abutting the sensing element; a conductive bottom surface abutting the sensing element; a ribbon comprising: a trace; and a conductive shield; wherein the ribbon is coupled to the sensor; the trace is insulated from conductive shield; the trace is coupled to either the conductive top surface or the conductive bottom surface; the sensor is configured to conform to a shape of an eye; and a flexural rigidity of the ribbon assembly is less than or equal to $10 \times 10^{-4}$ lbs-in$^4$.

An apparatus can comprise comprising: a detector comprising: a sensor comprising: a sensing element; a conductive top surface abutting the sensing element; a conductive bottom surface abutting the sensing element; a ribbon comprising: a trace; and a conductive shield; wherein the ribbon is coupled to the sensor; the trace is insulated from conductive shield; the trace is coupled to either the conductive top surface or the conductive bottom surface; the sensor is configured to conform to a shape of an eye; and thickness of the ribbon is less than or equal to 25 micrometers.

A method comprising: providing an eye sensor as described herein; applying a sensor to a patient's eyelid; sedating the patient; monitoring output from the display; adjusting anesthetic administered to the patient.

An apparatus comprising: an eye sensor comprising: a detector comprising a sensor electrically coupled to a ribbon; an amplifier; a processor configured to process signals received from the amplifier to obtain a result; and a display configured to display a result; wherein the eye sensor is electrically coupled to the amplifier; the amplifier is in communication with the processor; and the processor is in communication with the display.

An apparatus comprising: an eye sensor comprising: a sensor comprising: a sensing element; a conductive top surface abutting the sensing element; a conductive bottom surface abutting the sensing element; a ribbon comprising: a first trace; and a conductive shield; wherein the ribbon is coupled to the sensor; the first trace is insulated from conductive shield; the first trace is coupled to either the conductive top surface or the conductive bottom surface; an amplifier, electrically coupled to the ribbon comprising a printed circuit board, wherein the printed circuit board is configured to condition and amplify a signal; a processor configured to process the signal received from the amplifier to obtain one or more results; and a display configured to present the one or more results; wherein the eye sensor is electrically coupled to the amplifier; the amplifier is in communication with the processor; and the processor is in communication with the display. The sensing element can comprise a piezoelectric element. The sensing element can comprise multiple piezoelectric elements. The sensing element can comprise an arm actuator. The sensing element can comprise a piezoelectric element, and the piezoelectric element defines a tubular shape; the conductive top surface is located inside the piezoelectric element; and the conductive bottom surface is outside the piezoelectric element. The conductive shield can comprise a top shielding layer and a bottom shielding layer. The ribbon can further comprise a second trace that is insulated from conductive shield; the second trace is coupled to either the conductive top surface or the conductive bottom surface that is not coupled to the first trace. The conductive top trace or the conductive bottom trace can be electrically coupled to the conductive shield. The conductive shield can comprise a top shielding layer and the top shielding layer that extends to cover the sensor. The conductive shield can extend to cover the sensor. The ribbon can further comprise a terminal end, and the terminal end comprises an attachment and a terminal; wherein the attachment is electrically coupled to the attachment and the terminal is electrically coupled to the first trace. The ribbon can comprise a terminal end, and it is the terminal end of the ribbon that is coupled to the amplifier. The amplifier can further comprise a housing electrically coupled to the conductive shield. The amplifier can further comprise an amplifier grounding electrode that is configured to ground the amplifier when in contact with a patient's skin. The amplifier can further comprise an adhesive patch that is electrically conductive. The amplifier can be electrically coupled to the processor. The amplifier can further comprise a wireless transmitter and the processor comprises a wireless receiver. The result can comprise a frequency a combined data; wherein the frequency is ocular microtremors (OMT) frequency and the combined data comprises combined microsaccades (MS) amplitude and OMT amplitude, combined MS and OMT power, combined MS reactivity and OMT reactivity, or a combination thereof. The result can comprise a frequency and a combined data; wherein the frequency is ocular microtremors (OMT) frequency and the combined data comprises combined microsaccades (MS) amplitude and OMT amplitude, combined MS and OMT power, combined MS and OMT reactivity, or a combination thereof. The one or more results can comprise: a frequency and a combined data; wherein the frequency is ocular microtremors (OMT) frequency and the combined data comprises combined microsaccades (MS) amplitude and OMT amplitude, combined MS and OMT power, combined MS and OMT reactivity, or a combination thereof; and an event defined by the frequency and the combined data. The one or more results can further comprise an evaluation of the event. The one or more results can comprise: a frequency and a combined data; wherein the frequency is ocular microtremors (OMT) frequency and the combined data comprises combined microsaccades (MS) amplitude and OMT amplitude, combined MS and OMT power, combined MS and OMT reactivity, or a combination thereof; and a comparison of the frequency, the combined data, or the frequency and combined data to other values. The display can be configured to present the one or more results one or more screens. The display is further configured to present the one or more results on one or more monitors. The display can be further configured to present the one or more results on the same screen. The one or more results can comprise two or more results and the two or more results are contemporaneously with each other.

A method can comprise: receiving output signals from a sensor, wherein the sensor produces the output signals in response to eye movements; generating a frequency component and an amplitude component; wherein the frequency component comprises an ocular microtremor (OMT) frequency, the amplitude component comprises a microsaccades (MS) amplitude, and the OMT frequency and the MS amplitude are obtained from the output signals; and producing a combined data set from the frequency component and the amplitude component, wherein the combined data set comprises the frequency component, the amplitude component, and a time relationship between the frequency component and the amplitude component. The amplitude component further comprises an OMT amplitude, and the OMT amplitude is obtained from the output signals. The method can further comprise comparing the combined data set to at least one pre-known reference value to obtain a comparison. The method can further comprise producing a reference value; wherein the reference value is based on the combined data set, the comparison or a combination of the combined data set and the comparison. The sensor can sense eye movement through an eyelid. The method can further comprise creating output signals, wherein the creating the output signals comprises: producing voltage in response to eye movement by a piezoelectric element; and transmitting a current along an electrical connection. The method can further comprise amplifying the output signals to render amplified output signals, and the generating the frequency component and the amplitude component comprises processing the amplified output signals. The generating the frequency component and the amplitude component can comprises: processing the output signals by a processor; wherein the processing the output signals comprises: isolating eye movement attributed to OMT and MS, determining the frequency of the OMT, and determining a combined OMT MS amplitude, MS power, MS reactivity, or a combination thereof. The method can further comprise displaying results, wherein the displaying results comprise presenting a representation of the frequency component and the amplitude component, the combined data set, a reactivity of MS amplitude, or a combination thereof. The method can further comprise comparing the frequency component, the amplitude component, the combined data set, or combination thereof, to pre-known values, pre-known patterns, or both pre-known values and pre-set patterns. The method can further comprise displaying an alert or suggested action based upon the comparing. The method can further comprise event detection and event evaluation; wherein an event evaluation comprises determining a reactivity of an event, long term and short term ratios, before-during- and after event comparative analyses, frequency numbers, or a combination thereof.

A method can comprise: receiving output signals from a sensor, wherein the sensor produces the output signals in response to eye movements; deriving an ocular microtremor (OMT) component and a parameter comprising a microsaccades (MS) component; wherein the OMT component and the parameter are obtained from the output signals; and producing a combined data set from the OMT component and the parameter; wherein the OMT component is derived from OMT frequency, OMT amplitude, OMT speed, or a combination thereof; and the parameter is derived from MS frequency, MS amplitude, MS speed, or a combination thereof; and the combined data set incorporates the OMT component, the parameter, and a time relationship between the OMT component and the parameter. Wherein the OMT component can be derived from OMT frequency. The method can further comprise comparing the combined data set to at least one pre-known reference value to obtain a comparison. The method can further comprise producing a reference value; wherein the reference value is based on the combined data set, the comparison or a combination thereof. The method can have the sensor sense eye movement through an eyelid. The method can further comprise creating output signals, wherein the creating the output signals comprises: producing voltage in response to eye movement by a piezoelectric element; and transmitting a current along an electrical connection. The method can further comprise amplifying the output signals to render amplified output signals, and the deriving the OMT component and the parameter comprise processing the amplified output signals. The deriving the OMT component and the parameter can comprise: processing the output signals by a processor; wherein the processing the output signals comprises isolating eye movement attributed to OMT frequency of the OMT. The method can further comprise displaying results, wherein the displaying results comprise resenting a representation of the OMT component, the parameter, the combined data set, reactivity, or a combination thereof.

An ocular micro tremor (eye) sensor responsive to fixational eye movements of an eyeball of an individual which have an amplitude of an eyeball arc length excursion between 0.1 and 400 micrometers for providing an indication of the brain stem activity of the individual, said eye sensor can comprise an electrically active sensing element capable of converting said fixational eye movements to an electrical biosignal, said electrically active sensing element being attached to the skin of the individual so that said sensing element conforms to the shape of the individual's eyelid in order to receive the fixational eye movements of the individual's eyeball by way of the eyelid and generate said electrical biosignal in response to said fixational eye movements. The electrically active sensing element can comprise at least one flexible piezoelectric layer having an upper surface and a lower surface, a first electrically conductive material on said upper surface and a second electrically conductive material on said lower surface, said electrically active sensing element being attached to and conforming to the shape of the eyelid of the individual such that the flexible piezoelectric layer of said sensing element is in receipt of and deflected by the fixational eye movements of the individual's eyeball by way of his eyelid, whereby said electrical biosignal is generated between said first and second electrically conductive materials on the upper and lower surfaces of the flexible piezoelectric layer of said electrically active sensing element in response to the deflections of said flexible piezoelectric layer caused by said fixational eye movements. The eye sensor can include a flexible ribbon assembly electrically connected to said electrically active sensing element to receive the biosignal generated thereby, said flexible ribbon assembly comprising an upper layer having a first electrically conductive trace running therealong and a lower layer having a second electrically conductive trace running therealong, said first electrically conductive trace making electrical contact with the first electrically conductive material on the upper surface of said flexible piezoelectric layer of said electrically active sensing element, and said second electrically conductive trace making electrical contact with the second electrically conductive material on the lower surface of said flexible piezoelectric layer of said electrically active sensing element. The eye sensor can comprise an adhesive patch attached to the lower layer of said flexible ribbon assembly by which said flexible ribbon assembly is adhesively attached to the skin of the individual. Each of the upper and lower layers of said flexible ribbon assembly can be manufactured from a non-conductive material and has a top and a bottom, said first electrically conductive trace running along the bottom of said upper non-conductive layer, and said second electrically conductive trace running along the top of said lower non-conductive layer, said upper non-conductive layer located above said lower non-conductive layer and said first and second electrically conductive traces being electrically isolated from one another along said upper and lower non-conductive layers. Each of the top of said upper non-conductive layer and the bottom of said lower non-conductive layer of said flexible ribbon assembly can have an electrically conductive electromagnetic shielding surface located thereon, said electrically active sensing element and the first and second electrically conductive traces running along respective ones of the upper and lower non-conductive layers of said flexible ribbon assembly being surrounded by said electrically conductive shielding surfaces. The electrically conductive electromagnetic shielding surfaces located on the top of said upper non-conductive layer and the bottom of said lower non-conductive layer of said flexible ribbon assembly can be connected to each other and grounded at the skin of the individual. The flexible ribbon assembly can also comprise a first electrically conductive pad located between a first end of said first electrically conductive trace and the first electrically conductive material on the upper surface of the flexible piezoelectric layer of said electrically active sensing element and a second electrically conductive pad located between a first end of said second electrically conductive trace and the second electrically conductive material on the lower surface of the flexible piezoelectric layer of said electrically active sensing element. The upper and lower non-conductive layers of said flexible ribbon assembly can be retained one above the other such that said electrically active sensing element and said first and second electrically conductive pads are located, in some embodiments sandwiched, between the first end of the first electrically conductive trace which runs along the bottom of said upper non-conductive layer and the first end of the second electrically conductive trace which runs along the top of said lower non-conductive layer. The flexible ribbon assembly also comprising a third electrically conductive pad located between the opposite end of said first electrically conductive trace and a first output terminal of said flexible ribbon assembly, and a fourth electrically conductive pad located between the opposite end of said second electrically conductive trace and a second output terminal of said flexible ribbon assembly, such that the first and second electrically conductive materials laying on respective ones of the upper and lower surfaces of the flexible piezoelectric layer of said electrically active sensing element are electrically connected to respective ones of the first and second output terminals of said flexible ribbon assembly by way of said first and second electrically conductive traces, whereby said electrical biosignal is supplied from said electrically active sensing element to said first and second output terminals. The third electrically conductive pad can be located, in some embodiments sandwiched, between the opposite end of said first electrically conductive trace and the first output terminal of said flexible ribbon assembly, and the fourth electrically conductive pad is located, in some embodiments sandwiched, between the opposite end of said second electrically conductive trace and the second output terminal of said flexible ribbon assembly. The eye sensor can also include an eye signal amplifier having signal amplifying circuitry and a grounding electrode connected to electrical ground at the individual's skin, said flexible ribbon assembly connected between said electrically active sensing element and said eye signal amplifier by which to supply the electrical biosignal generated by said electrically active sensing element to said eye signal amplifier at which to be amplified by the signal amplifying circuitry thereof. The eye signal amplifier can also have a housing to enclose said signal amplifying circuitry and an electrically conductive adhesive patch by which said housing is adhesively attached to the skin of the individual. The housing of said eye signal amplifier can is manufactured from an electrically conductive electromagnetic shielding material, said amplifier housing connected to electrical ground at the individual's skin by way of said grounding electrode. The eye signal amplifier can also have a wireless transmitter to transmit the electrical biosignal supplied to and amplified by the signal amplifying circuitry of said eye signal amplifier to a location that is remote from said eye signal amplifier over a wireless communication path. The first and second electrically conductive traces running along the upper and lower non-conductive layers of said flexible ribbon assembly can be electrically connected from respective ones of the first and second electrically conductive materials on the upper and lower surfaces of said flexible piezoelectric layer of said electrically active sensing element to the signal amplifying circuitry of said eye signal amplifier so as to supply the electrical biosignal generated by said electrically active sensing element to said circuitry for amplification. The eye signal amplifier can also have first and second electrically conductive cushion supports lying in electrical contact with respective ones of the electrically conductive electromagnetic shielding surfaces located on the top of said upper non-conductive layer and on the bottom of said lower non-conductive layer of said flexible ribbon assembly, said first and second electrically conductive cushion supports being electrically connected to one another and to electrical ground at the individual's skin by way of the grounding electrode of said eye signal amplifier.

A system for generating an electrical biosignal that is indicative of the brain stem activity of an individual, said system can comprise: a piezo-active sensing element to be attached to an eyelid of the individual at which to be responsive to fixational eye movements of an eyeball of the individual and thereby generate said electrical biosignal, said piezo-active sensing element having at least one flexible piezoelectric layer with a top and a bottom, a first electrically conductive material located on the top of said piezoelectric layer, and a second electrically conductive material located on the bottom of said piezoelectric layer, said flexible piezoelectric layer being deflected by the fixational eye movements of the individual's eyeball such that said biosignal is generated between the first and second electrically conductive materials located at the top and at the bottom of said flexible piezoelectric layer in response to the deflections thereof; an amplifier located on the skin of the individual to receive and amplify the electrical biosignal generated in response to the deflections of the flexible piezoelectric layer of said piezo-active sensing element; and a ribbon assembly having first and second non-conductive layers, each of said first and second non-conductive layers having a respective electrically conductive trace running therealong, the electrically conductive trace running along the first non-conductive layer of said ribbon assembly connected between said amplifier and the first electrically conductive material located on the top of the flexible piezoelectric layer of said piezo-active sensing element, and the electrically conductive trace running along the second non-conductive layer of said ribbon assembly connected between said amplifier and the second electrically conductive material located on the bottom of the flexible piezoelectric layer of said piezo-active sensing element. The electrically conductive traces of said ribbon assembly can run along one side of respective ones of said first and second non-conductive layers, each of the opposite sides of the first and second non-conductive layers of said ribbon assembly being covered by an electrically conductive electromagnetic shielding surface, the electrically conductive electromagnetic shielding surfaces at the opposite sides of said first and second non-conductive layers being connected to each other and to electrical ground at the skin of the individual. The electrical biosignal can be generated by the flexible piezoelectric layer of said piezo-active sensing element and amplified by said amplifier is an alternating voltage analog biosignal having a frequency over time, said system further comprising: an analog to digital converter to convert the analog biosignal to a digital biosignal; filters to eliminate any portion of the digital biosignal having an amplitude that exceeds a predetermined amplitude; and a display to show a representation of the digital biosignal.

A system for generating an electrical biosignal that is indicative of the brain stem activity of an individual, said system can comprise: a piezo-active sensing element to be attached to the individual's skin at which to be responsive to fixational eye movements of an eyeball of the individual and thereby generate said electrical biosignal in response to said fixational eye movements, said piezo-active sensing element having at least one flexible piezoelectric layer with a top and a bottom, a first electrically conductive material located on the top of said flexible piezoelectric layer, and a second electrically conductive material located on the bottom of said flexible piezoelectric layer, said flexible piezoelectric layer being deflected by the fixational eye movements of the individual's eyeball such that said electrical biosignal is generated between the first and second electrically conductive materials located on the top and on the bottom of said flexible piezoelectric layer in response to the deflections thereof; and an amplifier to be attached to the individual's skin to receive and amplify the electrical biosignal generated as a result of the deflections of the flexible piezoelectric layer of said piezo-active sensing element. The flexible piezoelectric layer of said piezo-active sensing element is attached to an eyelid of the individual to conform to the shape of the eyelid in order to receive and be deflected by the fixational eye movements of the individual's eyeball by way of the eyelid. The electrical biosignal received and amplified by said amplifier can be an analog voltage biosignal, said system also comprising an analog to digital converter to convert the analog voltage biosignal to a digital biosignal; filters which eliminate any portion of the digital voltage biosignal which has an amplitude that exceeds a predetermined amplitude; and a display to show a representation of the digital biosignal. The system can further comprise a transceiver and wherein said amplifier comprises a wireless transmitter by which to transmit the amplified biosignal to said transceiver over a wireless communication path. The amplifier can communicate with the flexible piezoelectric layer of said piezo-active sensing element by means of a ribbon assembly having first and second non-conductive layers, each of the first and second non-conductive layers of said ribbon assembly having a respective electrically conductive trace running therealong, the electrically conductive trace running along the first non-conductive layer of said ribbon assembly connected between said amplifier and the first electrically conductive material located on the top of the flexible piezoelectric layer of said piezo-active sensing element, and the electrically conductive trace running along the second non-conductive layer of said ribbon assembly connected between said amplifier and the second electrically conductive material located on the bottom of the flexible piezoelectric layer of said piezo-active sensing element.

A method for generating an electrical biosignal that is indicative of the brain stem activity of an individual by means of an electrically active sensing element that is capable of converting fixational eye movements of an eyeball of the individual which have an amplitude of an eyeball arc length excursion between 0.1 and 400 micrometers into the electrical biosignal, said method can comprise the steps of attaching said electrically active sensing element to an eyelid of the individual so that said sensing element conforms to the shape of the eyelid in order to receive the fixational eye movements of the individual's eyeball through the eyelid. The method can comprise the additional step of amplifying the electrical biosignal generated by means of said electrically active sensing element. The method can comprising the additional steps of amplifying the electrical biosignal by means of an amplifier; locating the amplifier on the individual's skin; transmitting the amplified electrical biosignal from said amplifier to a signal processor over a wireless communication path; and comparing the amplified electrical biosignal with a known reference signal. The electrically active sensing element comprises at least one flexible piezoelectric layer having an upper surface and a lower surface, a first electrically conductive material located on said upper surface and a second electrically conductive material located on said lower surface, the flexible piezoelectric layer of said electrically active sensing element can be attached to and conforming to the shape of the eyelid of the individual such that said flexible piezoelectric layer is in receipt of and deflected by the fixational eye movements of the individual's eyeball, said method comprising the additional steps of: generating the electrical biosignal between the first and second electrically conductive materials located on the upper and lower surfaces of the flexible piezoelectric layer of said electrically active sensing element; amplifying the electrical biosignal by means of an amplifier attached to the individual's skin; supplying the electrical biosignal from said electrically active sensing element to said amplifier by way of a ribbon assembly having first and second non-conductive layers, wherein each of the first and second non-conductive layers of said ribbon assembly has an electrically conductive trace running therealong, the electrically conductive trace running along the first non-conductive layer of said ribbon assembly connected between said amplifier and the first electrically conductive material located on the upper surface of the flexible piezoelectric layer of said electrically active sensing element, and the electrically conductive trace running along the second non-conductive layer of said ribbon assembly connected between said amplifier and the second electrically conductive material located on the lower surface of the flexible piezoelectric layer of said electrically active sensing element. The method can comprise the additional steps of: covering the first non-conductive layer of said ribbon assembly with a first electromagnetic shielding material which lies opposite the electrically conductive trace running along said first non-conductive layer; and covering the second non-conductive layer of said ribbon assembly with a second electromagnetic shielding material which lies opposite the electrically conductive trace running along said second non-conductive layer, said first and second electromagnetic shielding materials surrounding said ribbon assembly so as to be electrically isolated from and enclose the electrically conductive traces running along the first and second non-conductive layers of said ribbon assembly and the first and second electrically conductive materials located on the upper and lower surfaces of the flexible piezoelectric layer of said electrically active sensing element.

BRIEF DESCRIPTION OF THE DRAWINGS

FIG. 14 is a top view of the shielded flexible ribbon assembly of FIG. 13 connected at a proximal end thereof to the multiple layer piezoelectric element of FIGS. 8-10 and at a terminal end to an electrical connector block of the eye signal amplifier of FIG. 12.

FIG. 15 is a cross-section of the shielded flexible ribbon assembly taken along lines 15-15 of FIG. 14.

FIG. 16 is a cross-section of the shielded flexible ribbon assembly taken along lines 16-16 of FIG. 14.

DETAILED DESCRIPTION

Figure 1:
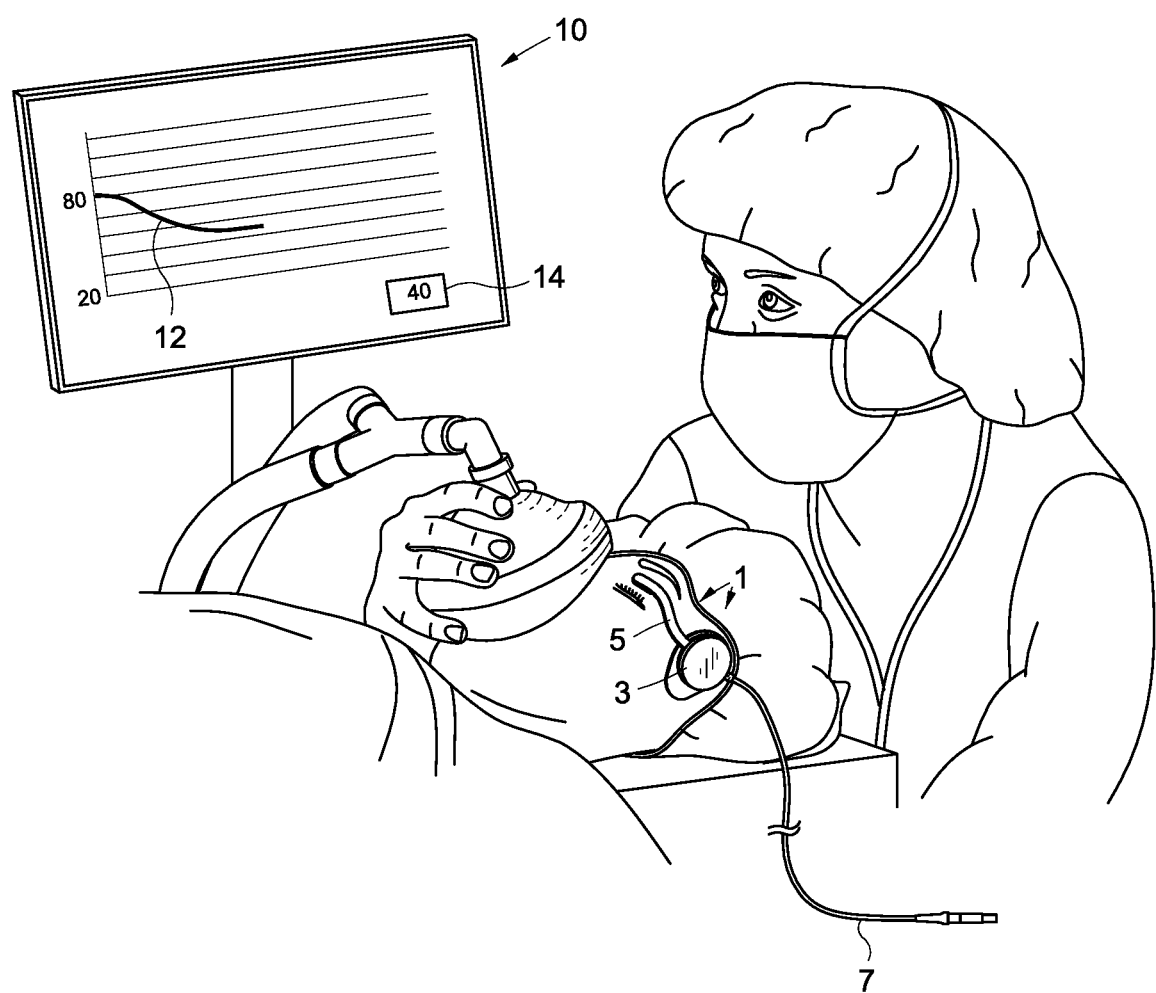
FIG. 1 shows an anesthesiologist watching an embodiment of a display to view graphical and numerical representations of an electrical biosignal which are indicative of the brain stem activity and level of consciousness of a sedated patient who undergoes an operation while wearing the eye sensor.

It will be appreciated that for simplicity and clarity of illustration, where appropriate, reference numerals and/or names have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein. It should be noted that references to "an" or "one" embodiment in this disclosure are not necessarily to the same embodiment, and such references mean at least one.

Several definitions that apply throughout this disclosure will now be presented.

The term "coupled" is defined as connected, whether directly or indirectly through intervening components and is not necessarily limited to physical connections. The connection can be such that the objects are permanently connected or releasably connected. The term "electrically coupled" is defined as being in structural electrical contact, whether directly or indirectly through intervening components, to allow the flow of electrons between the respective elements. The connection can be such that the objects are also "coupled". The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like.

Figure 25:
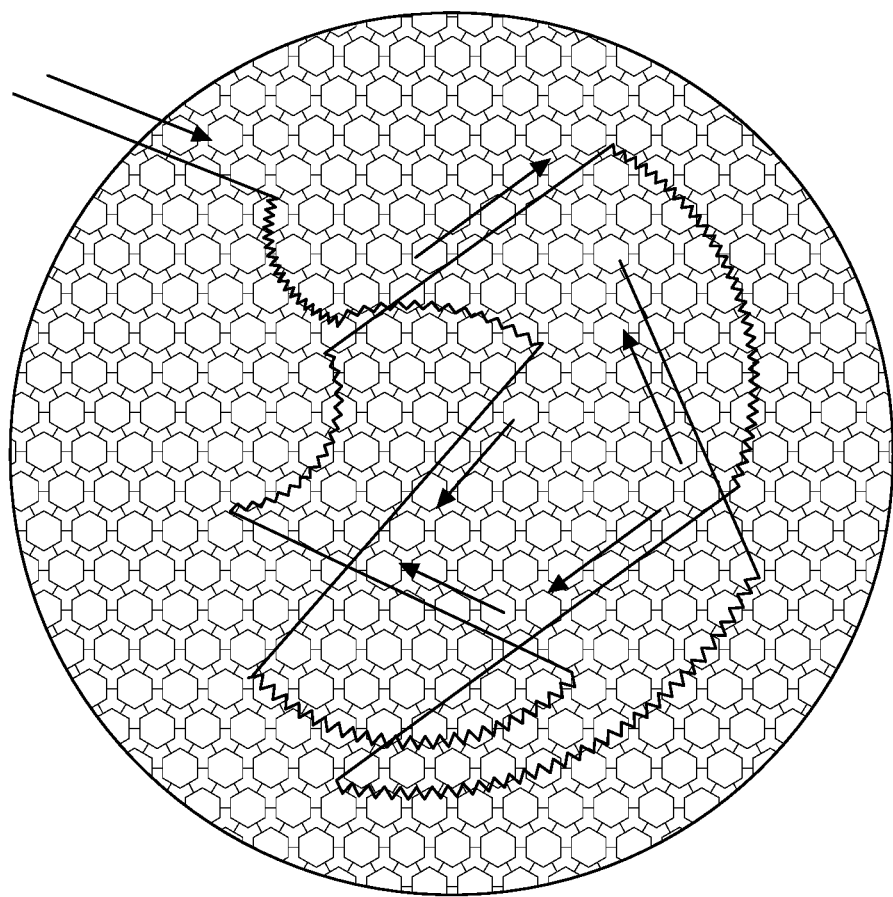
FIG. 25 shows a representation of fixational eye movements within a circle having a 25 micrometer radius.

As can be seen in FIG. 25, a representation of the fixational eye movements. To give scale, the radius of the circle is just 25 micrometers, approximately the size of one human hair. The eye is typically always moving about. The larger movements are drift and MS. The drift is a very slow movement, while the long, quick and substantially linear movements are the MS. The OMT and the drift occur at the same time. Ocular drift is the fixational eye movement characterized by a smoother, slower, roaming motion of the eye. The exact movement of ocular drift is often compared to Brownian motion, which is the random motion of a particle suspended in fluid as a result of its collision with the atoms and molecules that comprise that fluid. The movement can also be compared to a random walk, characterized by random and often erratic changes in direction. Although the frequency of ocular drifts is usually lower than the frequency of OMT (from 20 to 40 Hz compared to from 40 to 100 Hz), it is problematic to distinguish ocular drifts and ocular microtremors in the range from 30 to 40 Hz. Resolution of intersaccadic eye movements is technically challenging. The OMT are small, quick, and synchronized oscillations of the eyes occurring at frequencies in a range of 40 to 100 Hz, although they typically occur at around 90 Hz in the average healthy individual. The MS, also known as "flicks", are saccades, involuntarily, produced during the fixation periods. They are the largest and fastest of the fixational eye movements.

Referring initially to FIG. 1 of the drawings, there is shown a monitor such as healthcare practitioner, an anesthesiologist, intensivist, clinician, or the like, monitoring a patient who is unconscious and sedated. The monitor is able to acquire eye signal information, process it with preprogrammed routines, store and display multiple parameters simultaneously. The monitor is able to determine the brain stem activity and altered brainstem state of the patient to measure his level of sedation, consciousness, and responsiveness by virtue of a compact, low cost and highly compliant eye sensor 1. The eye sensor 1 is shown in FIG. 1 positioned at the eyelid 20 of the patient so as to be advantageously able to reliably sense the fixational eye movements of the patient's eyeball in order to provide the monitor with an indication of the patient's awareness during a medical procedure (e.g., in an operating room or intensive care facility). Fixational eye movements are present always (except on death and a few rare conditions) even when the eyes are apparently at rest, and occur involuntarily. Similarly, the body is nearly always undergoing stimulation, whether from the outside world, exogenously, or whether from within the body, endogenously. For example, hypoxic stimuli, which originate in the periphery, facilitate cardiopulmonary regulation and are processed continuously by the brainstem. Since the brainstem is constantly stimulated and since the fixational movements are always present, we can employ microsaccades and OMT and combinations thereof through the use of this invention productively in nearly all clinical and behavioral conditions.

However, it is to be understood that the eye sensor 1 herein disclosed can also be used to monitor and provide an indication of the alertness, awareness, arousal, diagnosis of injury and behavior modification of an individual in both medical and industrial environments. The eye sensor 1 also is also capable of monitoring any condition or circumstance in which it is desirable to obtain a measurement of brain stem activity of an individual to be compared against a known reference. To this end, the eye sensor 1 of this invention is advantageously capable of being attached directly over the patient's closed eyelid or in the tissue folds adjacent the patient's eyelid. While the eye sensor 1 will sometimes be referred to herein as having particular application for use by a patient in the care of a monitor or similar healthcare practitioner, it is to be once again understood that the eye sensor 1 can also be used in an industrial or other non-medical environments to test the alertness of one wishing to drive, operate machinery, perform complex tasks, etc.

The eye sensor 1 of FIG. 1 comprises a detector 11 and an amplifier 3. The detector 11 comprises a sensor (designated 16 in FIGS. 8-10). In some embodiments, the sensor 16 (designated 16 in FIGS. 8-10) comprises a multi-layer piezoelectric element that is electrically coupled to an amplifier 3 by way of a ribbon 5. The output of the amplifier 3 is supplied to a signal processor 9 (best shown in FIG. 17) by means of a shielded cable 7. The signal processor 9, in turn, is electrically connected to a visual display 10. The details of the sensor 16, the ribbon 5, as well as the amplifier 3 to which the sensor 16 is coupled to form the eye sensor 1 will be described in greater detail hereinafter.

FIG. 1 shows an embodiment of the visual display 10 which communicates with the signal processor 9 (of FIG. 17) to display information generated by the eye sensor 1. The display 10 can also provide information during a preliminary baseline test and/or when the patient is semi-conscious or fully conscious, alert and not sedated. By way of example only, the display 10 shows a fixational eye movement biosignal 12 that is generated by the eye sensor 1 in response to fixational eye movements of the patient's eyeball. The shape and amplitude/power/reactivity of the fixational eye movement biosignal 12 provide a graphical representation of the patient's brain stem activity and his level of consciousness over a particular sampling time. The fixational eye movements comprise of MS and OMT. The OMT biosignal is generally an alternating voltage waveform that is reflective of the OMT of the patient's eyeball to which the eye sensor 1 is responsive by way of the patient's eyelid. The combined OMT/MS power reactivity signal tends to be erratic and eventful, with long steady calm periods interrupted by the rapid onset of steep increases, peaks, and valleys.

In addition, the display 10 also shows a discrete reference number 14 to be computed by the signal processor 9 for easy visual reference by the monitor. By way of example, the reference number 14 being displayed is dependent upon the fixational eye movements of the eyeball and the corresponding frequency of the waveform of the fixational eye movement biosignal 12 in order to provide another indication of the patient's brain stem activity and his level of consciousness, sedation, and responsiveness.

Figure 2:
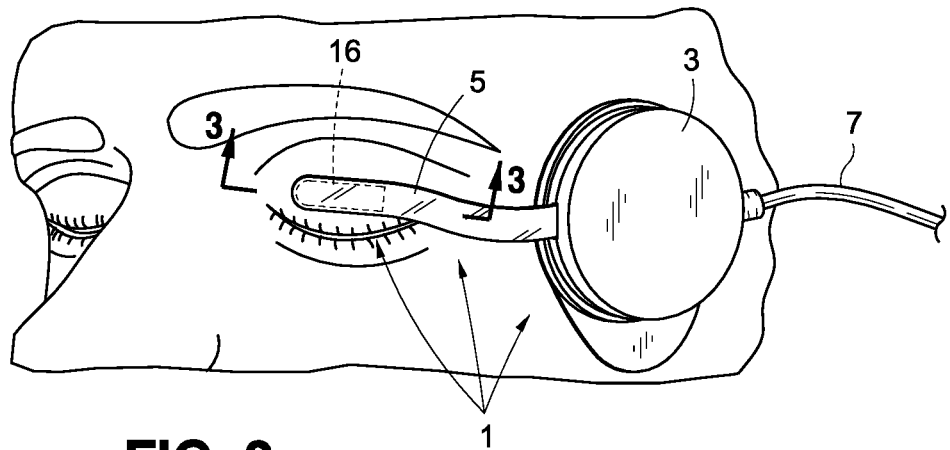
FIG. 2 shows an embodiment of a multiple layer piezoelectric element of the detector of FIG. 1 attached to a closed eyelid of the patient at which to be responsive to fixational eye movements of the patient's eyeball so that the biosignal is generated by the sensing element and supplied to an eye signal amplifier mounted at the eye.
Figure 3:
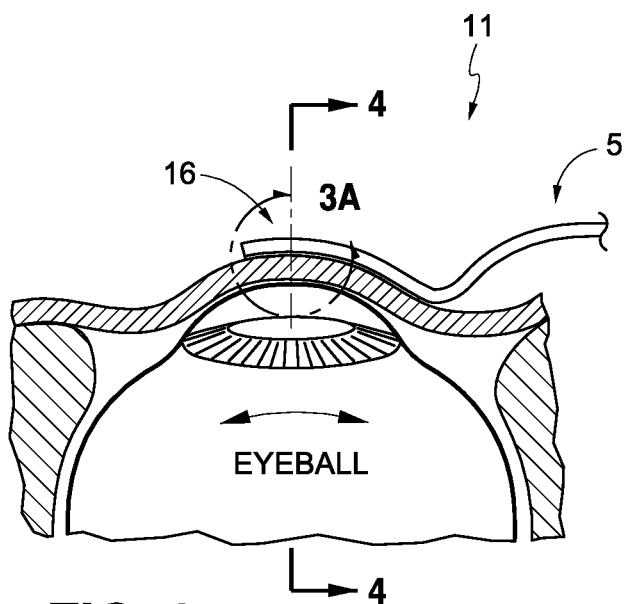
FIG. 3 is a cross-section of the detector taken along lines 3-3 of FIG. 2.
Figure 4:
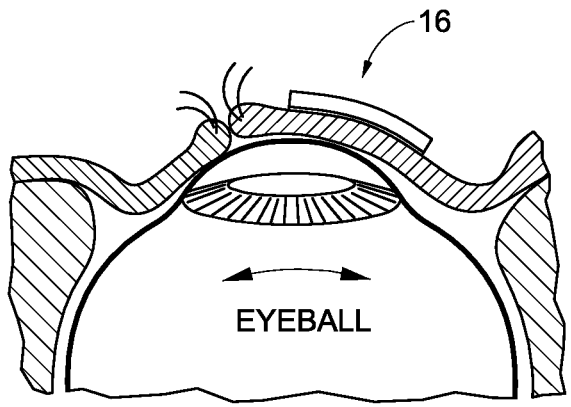
FIG. 4 is a cross-section of the eye detector taken along lines 4-4 of FIG. 3.

Turning now to FIGS. 2-4 of the drawings, an embodiment of the sensor 16 (of FIGS. 8-10) is shown attached to a closed eyelid of an individual, such as a patient who is heavily sedated while undergoing an operation in an operating room. However, and as indicated previously, the sensor 16 can also be attached to the eyelid of an individual undergoing evaluation in many settings (e.g. intensive care unit, industrial and other non-medical environments). In some embodiments, the patient's eyelid 20 is held closed prior to the attachment of the sensor 16. A double-sided pressure sensitive adhesive patch 100 (shown in in FIGS. 3A and 13) can be used to hold the sensor 16 against the patient's closed eyelid above the patient's eyeball at which to be responsive to the fixational eye movements of the eyeball and thereby provide the fixational eye movement biosignal 12 (of FIG. 1) by way of the ribbon 5 to the amplifier 3. The amplifier 3 provides an amplified analog signal of the fixational eye movement biosignal 12 to the signal processor 9 so that both graphical and numerical representations of the patient's brain stem activity including his level of consciousness, sedation, and responsiveness are visually available to the monitor on the display 10.

However, there are instances when it would be desirable to be able to use the eye sensor 1 to measure and indicate the patient's brain stem activity and his level of consciousness when his eyelid is fully or partially open. In this case, and referring to FIGS. 5 and 6 of the drawings, the eye sensor 1 is shown attached to the patient's rolled up eyelid. For example, the eye sensor 1 is shown being used in the manner shown in FIGS. 5 and 6 at those times when the patient is lightly, moderately or not sedated, when the patient's eyelid is alternately being opened and closed, or when the patient's eyelid is fully open, such as while a preliminary baseline test is being conducted.

Figure 5:
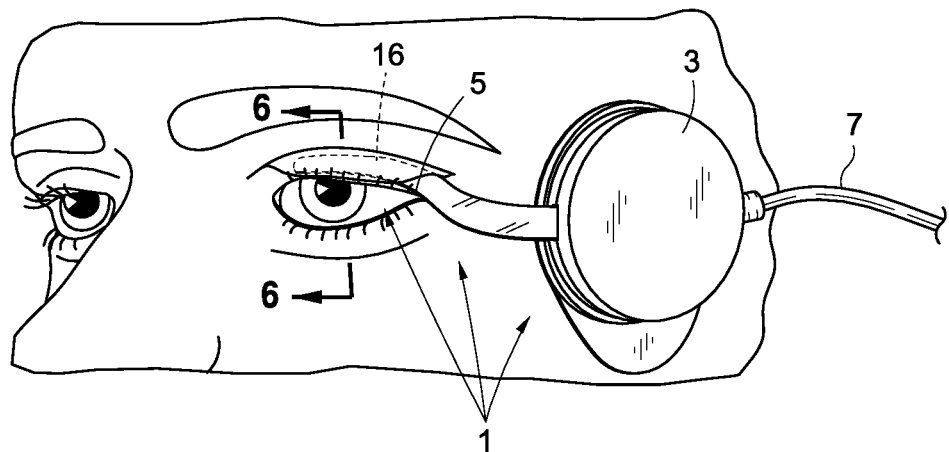
FIG. 5 shows an embodiment the piezoelectric element of the detector of FIG. 1 located within the tissue folds of the patient's open eyelid at which to be responsive to the fixational eye movements of the patient's eyeball so that the fixational eye movement biosignal is generated by the sensing element and supplied to the eye signal amplifier.
Figure 6:
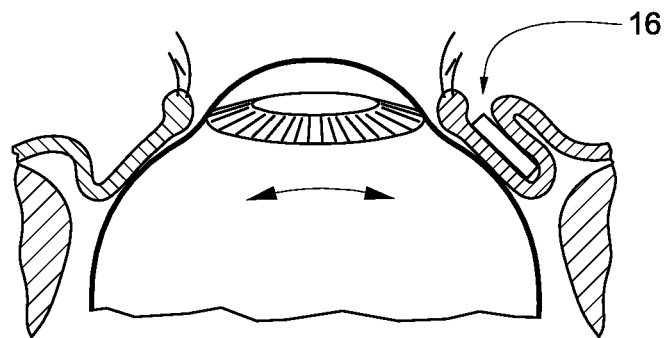
FIG. 6 is a cross-section of the detector taken along lines 6-6 of FIG. 5.

By virtue of the foregoing, the patient's brain stem activity and level of consciousness can be continuously monitored to enable intervention by the monitor or other healthcare practitioner when necessary. Because the eye sensor 1 including the sensor 16 (of FIGS. 8-10) and the ribbon 5 is thin and compliant, the sensor 16 may be advantageously attached, as shown in FIGS. 5 and 6, between the tissue folds of the patient's opened eyelid at which the sensor 16 of detector 11 is responsive to the fixational eye movements of the patient's eyeball.

Figure 7:
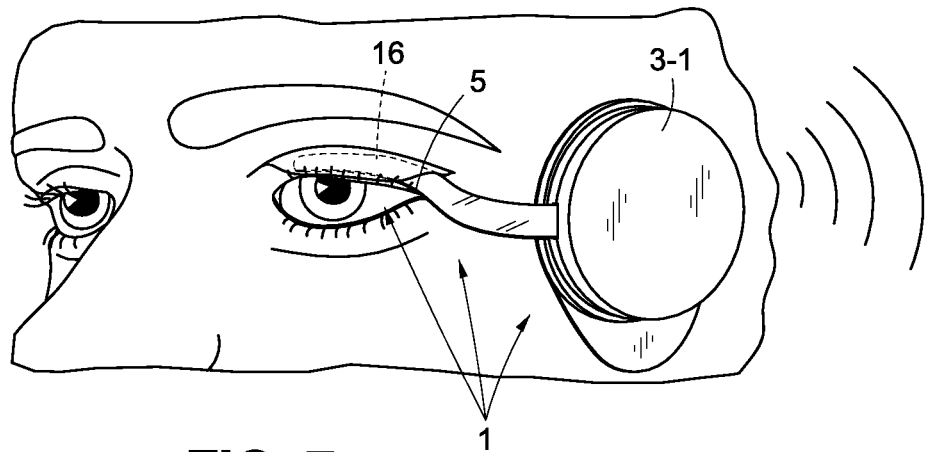
FIG. 7 shows the eye detector of FIG. 5 including a wireless eye signal amplifier.

In FIGS. 1-6, the amplifier 3 is shown as being connected to a signal processor (designated 9 in FIG. 17) by means of a shielded cable 7. However, as shown in FIG. 7 of the drawings, it is within the scope of this invention for the amplifier 3 to be replaced by a wireless eye signal amplifier 3-1. In this case, the shielded cable (designated 7 in FIG. 5) will now be eliminated. Moreover, in some embodiments, the wireless eye signal amplifier 3-1 is provided with an analog-to-digital converter (designated 110 in FIG. 18) and a conventional wireless transmitter (designated 116 in FIG. 18), and the signal processor (designated 9-1 in FIG. 18) is provided with a complimentary wireless transceiver 118. In this manner, the amplified fixational eye movement biosignal 12 can be transmitted from the amplifier 3-1 to the signal processor 9-1 at a remote location and over a wireless communication path.

Figure 8:
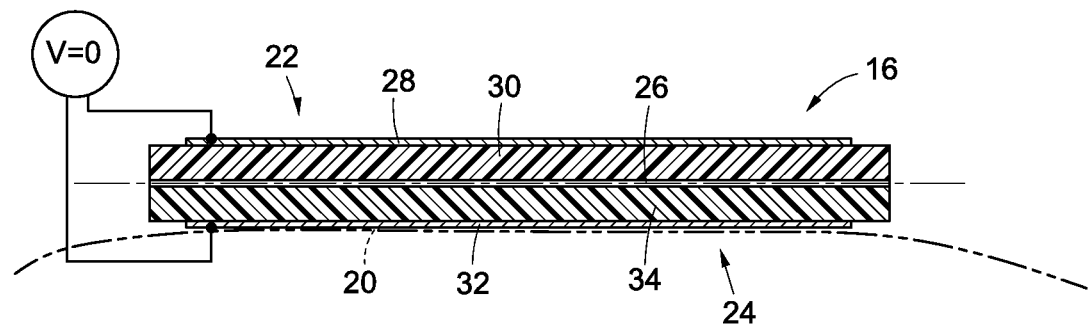
FIG. 8 shows an embodiment for the multiple layer piezoelectric element of the detector of FIG. 1 which is deflected in response to the fixational eye movements of the patient's eyeball to which the sensing element is responsive in order to generate the eye biosignal.
Figure 9:
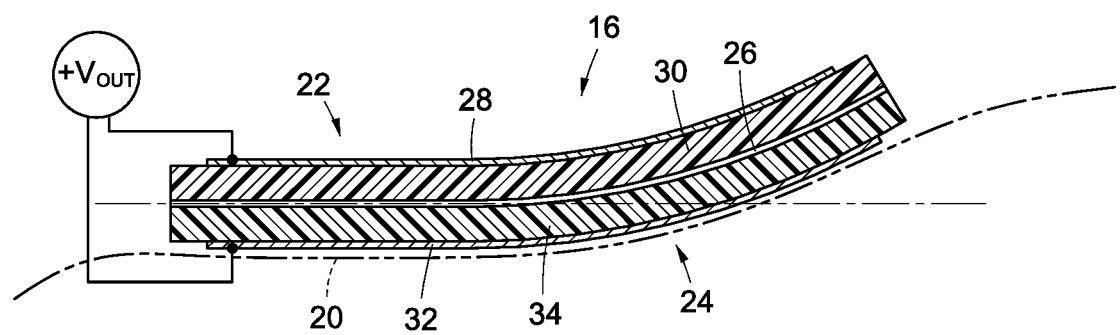
FIGS. 9 and 10 show an embodiment of the multiple layer piezoelectric element of FIG. 8 being deflected in different directions to generate the fixational eye movement biosignal depending upon the direction of the fixational eye movements of the patient's eyeball.
Figure 10:
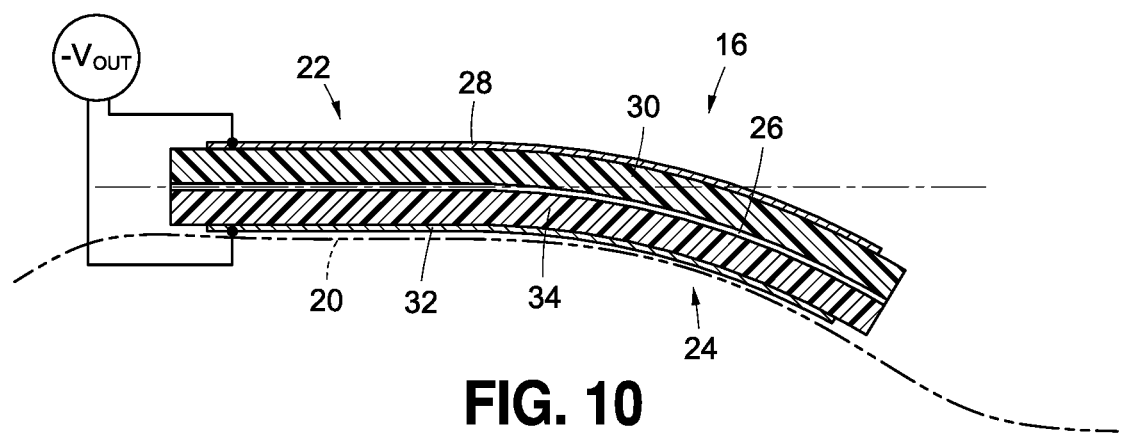

Details of an embodiment the sensor 16 shown in FIGS. 1-6 are now disclosed while referring to FIGS. 8-10 of the drawings. As was previously explained, the sensor 16 is held against the moving surface of the patient's opened or closed eyelid (represented generally by reference numeral 20 in FIGS. 8-10) so as to be responsive to the fixational eye movements of the patient's eyeball which have an amplitude of an eyeball arc length excursion between 0.1 and 400 micrometers and thereby provide a corresponding alternating voltage fixational eye movement biosignal to the soon-to-be-described eye signal amplifier (designated 3 in FIG. 1).

In some embodiments, an electrically conductive (e.g., copper) top surface 28 is applied to the top of the sensing element 30 to establish a first output terminal. An electrically conductive (e.g., copper) bottom surface 32 is applied to the bottom of the sensing element 30 to establish a second output terminal.

In some embodiments, the sensor 16 comprises a piezo-electric thin planar top layer 22, a thin planar bottom layer 24 and an intermediate bonding agent 26 (e.g., epoxy) located therebetween to form a layered-type structure. A first electrically conductive (e.g., copper) top surface 28 is applied to the outside of a flexible first piezoelectric (e.g., PVDF) film 30 from the top layer 22 of the sensor 16 to establish a first output terminal. An electrically conductive (e.g., copper) bottom surface 32 is applied to the outside of a flexible second piezoelectric film 34 from the bottom layer 24 of sensor 16 to establish a second output terminal. Each of the first piezoelectric film 30 and second piezoelectric film 34 of the top layer 22 and bottom layer 24 of sensor 16 which face one another are held in opposing alignment by the intermediate bonding agent 26. The length and width of the first piezoelectric film 30 and second piezoelectric film 34 may be larger than the respective length and width of the top surface 28 and the bottom surface 32 so as to avoid undesired electrical communication between the top surface 28 and bottom surface 32. In some embodiments, the thickness of the sensor 16 shown in FIGS. 8-10 is between 20 to 150 microns.

In some embodiments, the sensor 16 is able to generate a voltage as the sensing element is deflected in response to the fixational eye movements of the patient's eyeball which create a corresponding motion through the eyelid 20 above which the sensor 16 is attached. That is to say; the sensor 16 is deformed and deflected by the movements of the patient's eyelid 20 caused by the fixational eye movements of the eyeball. In the case where the sensor 16 is at rest as shown in FIG. 8, no voltage is generated by the sensor 16 between the first and second output terminals at the top surface 28 and bottom surface 32. In the case where the sensor 16 is deflected in a first direction by the movement of the patient's eyelid 20 in the same first direction as shown in FIG. 9, a positive voltage is generated by the sensor 16 between the output terminals at the top surface 28 and bottom surface 32. In the case where the sensor 16 is deflected in the opposite direction by the movement of the patient's eyelid 20 in the same opposite direction as shown in FIG. 10, a negative voltage is generated by the sensor 16 between the output terminals at the top surface 28 and bottom surface 32.

Because the fixational eye movements of the patient's eyeball typically occur at nanometer and micrometer levels across a range of frequencies and with variable intensity, the sensor 16 is designed to be flex back and forth at in like correspondence, so as to generate biosignals. The amplitude, positive or negative direction, and frequency of the fixational eye movements to which the sensor 16 is responsive are isolated, processed and re-integrated and reflected graphically in a time synchronized manner so as to illustrate various events and patterns and numerically by the displayed traces e.g. 12 and the summary reference values e.g. 14 that are visually accessible to the user on the display 10 of FIG. 1.

It is to be expressly understood while the sensor 16 is shown as comprising a pair of piezoelectric elements (the first piezoelectric film 30 and second piezoelectric film 34), in the drawings, it is disclosed that sensor 16 can comprise one or more piezoelectric elements, and the top and bottom thereof will have electrically conductive surfaces which lie thereon to establish the aforementioned first and second output terminals between which the fixational eye movement biosignal is generated. In some embodiments, the sensor 16 comprises a single piezoelectric element, in others, the sensor comprises of 3 or more piezoelectric elements.

Figure 3A:
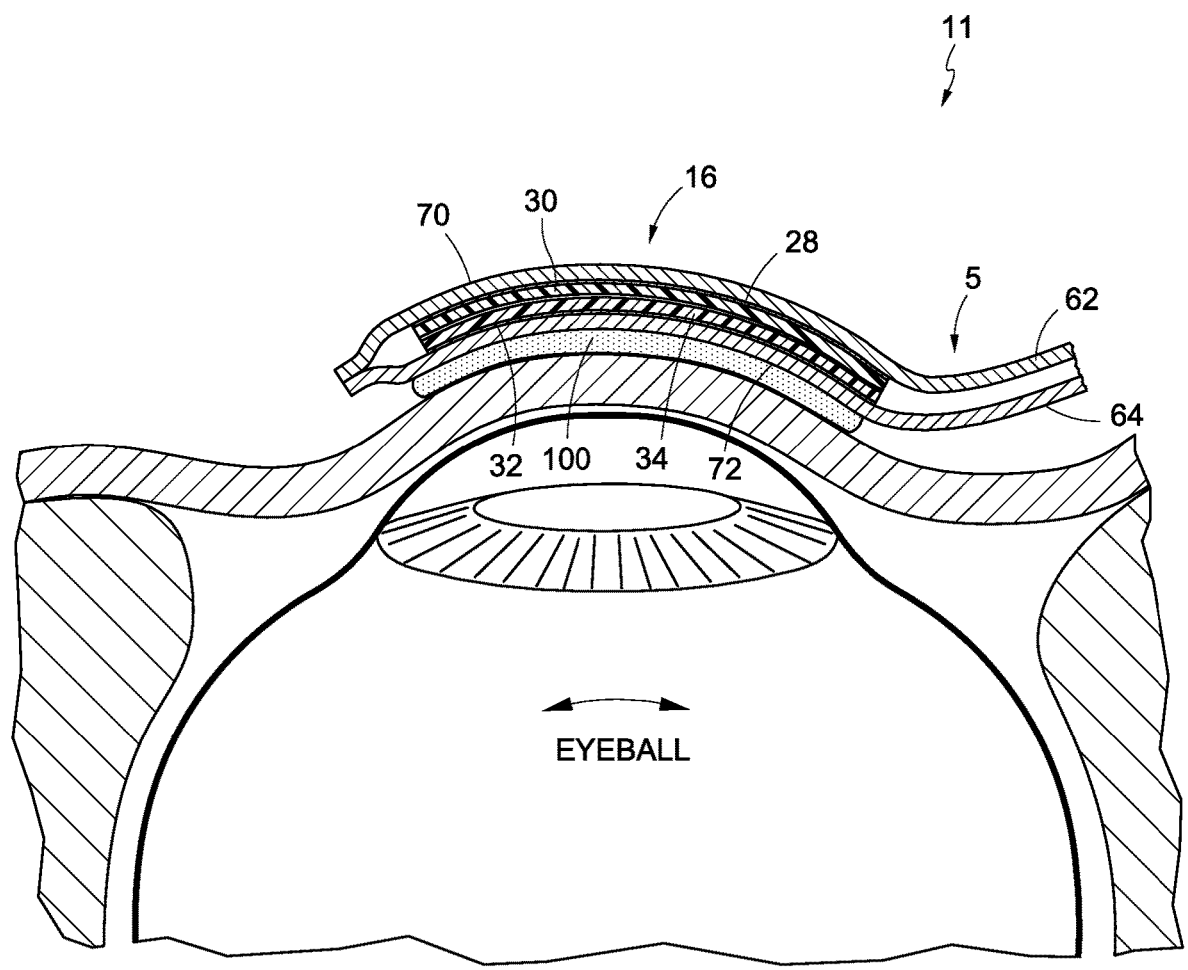
FIG. 3A is an enlarged detail taken from FIG. 3 showing a multiple layer piezoelectric element of the detector lying on the closed eyelid of the patient.

Referring specifically to FIGS. 3 and 3A of the drawings, a position is described in which the sensor 16 of the detector 11 shown in FIGS. 8-10 is held against the patient's fully closed eyelid. As an important feature of some embodiments, the sensor 16 is sufficiently thin (as explained when referring to FIGS. 8-10) and compliant to assume a generally arcuate (e.g., curved) configuration in order to conform to the shape of the patient's eyelid when the sensing element is attached thereto by means of the adhesive 100. The adhesive can be a double-sided pressure sensitive adhesive patch. In some embodiments, the sensor 16 surrounds at least some of the patient's closed eyelid and is sized so as to be large enough to cover angular excursions of the eyeball yet small enough to be placed within the eye socket.

In this regard, the sensor 16 of this can be sized such that it will cover a relatively large surface area of the eyelid so as to be responsive to a full range of motion of the patient's eyeball transmitted through the eyelid. Moreover, the pressure applied to the eyelid by the sensor 16 is more uniformly distributed around the eyelid than some conventional focused pressure sensing elements. Accordingly, the sensor 16 will be more comfortable to wear for longer periods, is less costly and easier to accurately position at the eyelid to achieve a reliable response than some conventional focused pressure sensing elements. Therefore, the eye sensor 1 can be comfortably fitted to the patient such that the sensor 16 thereof is unlikely to be noticed or objected to.

The sensor 16 is shown in FIG. 3A conforming to the shape of the patient's eyelid and being coupled to the ribbon 5. As will be described in greater detail when referring to FIGS. 16-18, the sensor 16 is surrounded by upper strip 62 and lower strip 64 of the ribbon 5. The top shielding layer 70 and the bottom shielding layer 72 lay over the outside surfaces of respective ones of the upper strip 62 and lower strip 64 to provide the ribbon 5 with shielding. The shielding will avoid subjecting the biosignal generated by the sensor 16 and transmitted via the ribbon 5 to electrical and electromagnetic noise and other interference.

Figure 11:
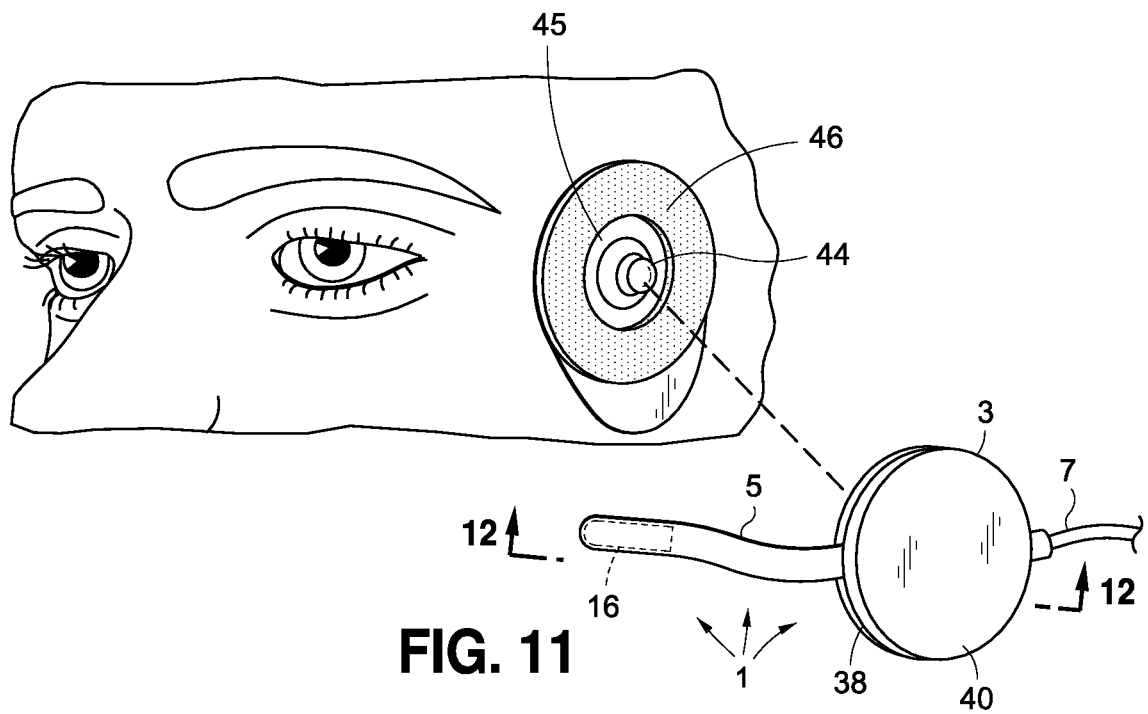
FIG. 11 shows the eye signal amplifier of the eye sensor of FIG. 2 being detachably connected to a grounding electrode that is attached by an electrically conductive adhesive patch to the patient's skin.
Figure 12:
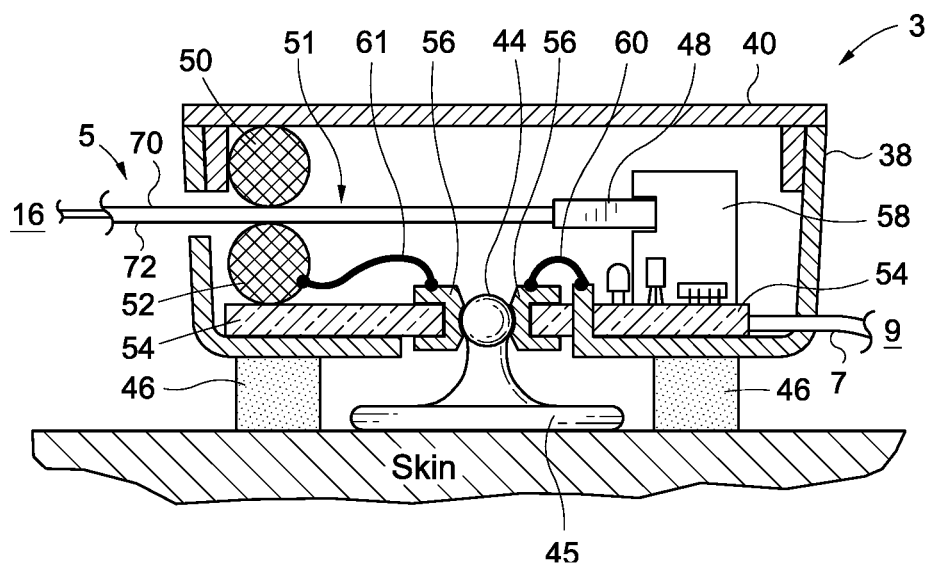
FIG. 12 is a cross-section of the eye signal amplifier taken along lines 12-12 of FIG. 11.

An embodiment of the amplifier 3 is described while referring to FIGS. 11 and 12. To isolate the electrical components of the amplifier 3 and thereby prevent environmental electrical and electromagnetic interference from altering the information contained by the eye biosignal, the amplifier 3 is provided with a conductive amplifier housing 38 having a removable lid 40. The sensor 16 is electrically connected to the amplifier 3 by way of the ribbon 5 (best shown in FIGS. 13-16).

When in use ribbon 5 can be of such a length that slack is present between the sensor 16 and the amplifier 3 so as to avoid applying loads or pulling forces to the patient's eyelid and thereby inducing a possible unintended response by the sensor 16.

In some embodiments, an amplifier grounding electrode 44 comprising a flat conductive base 45 is to abut the patient's skin. In some embodiments, an electrically conductive adhesive patch 46 (e.g., a common EKG electrode patch) attaches the bottom of the amplifier housing 38 to the patient. The amplifier 3 can be located near the sensor 16 so as to reduce the overall area of the ribbon cable but in a slack manner so as to avoid applying a pulling force against the ribbon 5. An electrical receptacle 56 inside the amplifier housing 38 is coupled to the amplifier grounding electrode 44. The adhesive patch 46 anchors the amplifier 3 in place and the conductive base against the patient's skin. The attachment helps prevent a displacement of the amplifier 3 relative to the ribbon 5 during monitoring. It should be recognized that other conventional electrical and mechanical (e.g., straps, glue, suction) amplifier attachment means can be substituted for the electrically conductive adhesive patch 46 just so that the amplifier is grounded.

To ensure that the amplified alternating voltage signals generated by the amplifier 3 are not altered by the environment, the electrically conductive amplifier housing 38, the top shielding layer 70, and the bottom shielding layer 72 can be electrically coupled to electrical ground. In some embodiments, electrical paths are established to ground from top shielding layer 70 and the bottom shielding layer 72 of the ribbon 5 and the amplifier housing 38 of the amplifier 3 to the patient's skin at the amplifier grounding electrode 44 which is held in place against the skin by the electrically conductive adhesive patch 46. In some embodiments, the electrically conductive amplifier housing 38, the top shielding layer 70, and the bottom shielding layer 72 are electrically coupled to a grounded item besides the patient. Details of these electrical paths to ground at the patient's skin are described below.

In the embodiment shown in FIG. 12, the ribbon 5 is connected at a proximal end thereof to the sensor 16 (best shown in FIG. 13) and at the terminal end 51 to an electrical connector block 48 that is located in the interior of the amplifier housing 38. A first electrically conductive (e.g., mesh) pillow 50 is positioned within amplifier housing 38 so as to lie between the removable lid 40 thereof and the top shielding layer 70 that runs over the top of the ribbon 5. A second electrically conductive pillow 52 is positioned within amplifier housing 38 so as to lie between the electrically conductive shielding 72 that runs over the bottom of the ribbon 5 and a printed circuit board 54 that is positioned at the bottom of the amplifier housing 38 of the amplifier 3. The aforementioned amplifier grounding electrode 44 is detachably connected to the amplifier 3 through the bottom of amplifier housing 38 and to the printed circuit board 54 at the electrical receptacle 56, such that the flat conductive base 45 of the amplifier grounding electrode 44 is connected to ground against the patient's skin.

In some embodiments, the amplifier 3 comprises first and second electrically conductive pillows 50 and 52 that lie in electrical contact with respective ones of the aforementioned electrically conductive top shielding layer 70 and the bottom shielding layer 72. Thus, the top shielding layer 70 at the top of the ribbon 5 is connected to ground at the patient's skin by way of a first electrical path to ground that comprises the first conductive pillow 50, the electrically conductive amplifier housing 38, a first jumper wire 60 that connects amplifier housing 38 to the electrical receptacle 56, and finally the amplifier grounding electrode 44 and the base 45 lying against the patient's skin. The bottom shielding layer 72 at the bottom of the ribbon 5 is also connected to ground by way of a second electrical path to ground that comprises the second conductive pillow 52 and a second jumper wire 61 that connects pillow 52 to the electrical receptacle 56, and finally the amplifier grounding electrode 44 and the base 45 thereof against the user's skin. In this same regard, it may be appreciated that top shielding layer 70 and the bottom shielding layer 72 at the top and bottom of the ribbon 5 are electrically connected to one another by way of the electrically conductive pillows 50 and 52 and the electrically conductive amplifier housing 38.

The resilient characteristic of the electrically conductive (e.g., mesh) pillows 50 and 52 which overlay the top shielding layer 70 and the bottom shielding layer 72 of the ribbon 5 accommodate and absorb bending forces to which the ribbon 5 is subjected. The pillows 50 and 52 also support the ribbon 5 within the amplifier housing 38 and suspend the ribbon 5 above the printed circuit board 54 so as to lie in axial alignment with the electrical connector block 48. The electrical connector block 48 to which the terminal end 51 of the ribbon 5 is connected is, in turn, electrically connected to the printed circuit board 54 by way of an upstanding connector post 58. The printed circuit board 54 contains conventional signal conditioning and amplifier circuitry by which the fixational eye movement biosignal is alternating voltage biosignal carried by the ribbon 5 is amplified, in some embodiments by a factor of at least ten. An amplified analog fixational eye movement biosignal is supplied from the amplifier 3, shown in FIG. 12, to the signal processor 9 and display 10, of FIG. 17, by means of the shielded cable 7 that extends from the printed circuit board 54. However, as earlier explained the fixational eye movement biosignal might also be transmitted from the amplifier 3 to the signal processor 9 over a wireless communication path illustrated in FIG. 18.

Referring concurrently to FIGS. 13-16 of the drawings, details are now provided of an embodiment of the ribbon 5, which is electrically connected at the proximal end thereof to the sensor 16 (previously described while referring to FIGS. 8-10) and at the opposite terminal end 51 to the amplifier 3 (as described while referring to FIG. 12). The ribbon 5 is disposed in surrounding engagement with and connected between the top surface 28 and bottom surface 32 of the sensor 16 and the electrical connector block 48 that is held, by the connector post 58, above the printed circuit board 54, that is positioned inside and at the bottom of the shielded housing 38 of the amplifier 3 shown in FIG. 12.

Some embodiments of the ribbon 5 comprise upper and lower elongated and upper strip 62 and lower strip 64 that are attached one above the other. By way of example, the bottom of the upper strip 62 and the top of the lower strip 64 can be bonded face-to-face one another by a conventional thin layer of adhesive (designated 65 in FIG. 15). Each of the upper and lower strips 62 and 64 of ribbon 5 comprises an upper non-conductive layer 66 and bottom non-conductive layer 68 that can be manufactured from an electrical insulating polyimide or any other suitable non-conductive material. Both the top and the bottom of each of the upper non-conductive layer 66 and the bottom non-conductive layer 68 of the upper and lower strips 62 and 64 are initially covered by an electrically conductive (e.g., aluminum or gold) coating.

As shown in the embodiment shown in FIG. 15, top shielding layer 70 and the bottom shielding layer 72 which cover the outwardly facing top of the upper non-conductive layer 66 of the upper strip 62 and the outwardly facing bottom of the bottom non-conductive layer 68 of the lower strip 64 of the ribbon 5 are left intact to create shielding surfaces. The top shielding layer 70 and the bottom shielding layer 72 were previously described while referring to FIG. 12 as being connected to each other and to ground at the individual's skin to shield the ribbon 5 against electrical and electromagnetic energy that might interrupt or distort the biosignal generated by the sensor 16 and supplied to the amplifier 3 by ribbon 5.

As shown in the embodiment shown in FIG. 13, portions of the shielding, which can initially cover the inwardly facing bottom of the upper non-conductive layer 66 of the upper strip 62 and the opposing inwardly facing top of the bottom non-conductive layer 68 of the lower strip 64, can be etched away to leave respective longitudinally extending electrically conductive traces 74 and 76 running along the upper non-conductive layer 66 and the bottom non-conductive layer 68 of the upper and lower strips 62 and 64. During the aforementioned etching process, pairs of relatively wide electrically conductive upper terminals 78, 79 and conductive lower terminals 80, 81 are formed at first and opposite ends of each of the conductive traces 74 and 76. With the upper and lower strips 62 and 64 of the ribbon 5 bonded together by the intermediate adhesive layer 65 (of FIG. 15), the longitudinally extending electrically conductive traces 74 and 76 formed on the bottom and on the top of the upper non-conductive layer 66 and the bottom non-conductive layer 68 lie in parallel alignment and in electrical isolation from one another. The aforementioned etching process is an example of a technique for forming the electrically conductive traces 74 and 76. However, it should be understood that other conventional techniques can be used to form the traces 74 and 76 on the upper non-conductive layer 66 and the bottom non-conductive layer 68.

As shown in the embodiment shown in FIG. 15, the sensor 16 can be a multi-layer piezo-active element and located, in some embodiments sandwiched, between first ends of the upper and lower strips 62 and 64 at the proximal end of the ribbon 5. In some embodiments, an electrically conductive upper pad 82 is adhesively bonded between the upper terminal 78 located at a first end of the upper trace 74, on the bottom of the upper strip 62, and the top surface 28, on the top of the sensor 16. An electrically conductive lower pad 83 is located between the bottom surface 32, which lies at the bottom of the sensor 16, and the lower terminal 80, located at a first end of the lower trace 76, on the top of the lower strip 64. The upper and lower terminals 78 and 80 at the first ends of traces 74 and 76 and the upper pad 82 and the lower pad 83, on the top and the bottom of the sensor 16, are all aligned with one another in a stack at the proximal end of the ribbon 5.

In some embodiments, an electrically conductive upper terminal pad 84 is adhesively bonded between the upper terminal 79 formed at the opposite end of the upper trace 74 on the bottom of the upper strip 62 and an opposing upper terminal 86 formed on the top of a flexible transition circuit board 88 (of FIG. 13). The circuit board 88 is located, in some embodiments sandwiched, between opposite ends of the upper strip 62 and lower strip 64 at the terminal end 51. An electrically conductive lower terminal pad 85 is located between the lower terminal 81, located at the opposite end of the lower trace 76 on the top of the lower strip 64, and an opposing lower terminal 90, located on the bottom of the flexible transition circuit board 88. The terminals 79 and 81, at the opposite ends of the upper trace 74 and the bottom trace 76, the upper terminal pad 84, the lower terminal pad 85, located above and below the circuit board 88, the opposing upper terminal 86 and the circuit board lower terminal 90, of the circuit board 88, are all aligned with one another in a stack at the terminal end 51 of the ribbon 5.

The upper terminal 86 of the transition circuit board 88 (e.g., a first output terminal of the ribbon 5) is electrically connected to the electrical connector block 48 that is surrounded by the electrically conductive shielded amplifier housing 38 (of FIG. 12) by way of a first conductive trace 92 lying on the top of circuit board 88 and a first electrical contact 94 of electrical connector block 48. The circuit board lower terminal 90 of the transition circuit board 88 (e.g., a second output terminal of the ribbon 5) is electrically connected to the electrical connector block 48 by way of a second conductive trace 96 lying on the bottom of circuit board 88 and a second electrical contact 98 of electrical connector block 48. As was previously explained while referring to FIG. 12, the electrical connector block 48 is electrically connected to the printed circuit board 54 that lies at the bottom of the amplifier housing 38 of amplifier 3. Therefore, it may be appreciated that the alternating voltage biosignal generated by the sensor 16 can be transmitted from the top surface 28 and bottom surfaces 32 at the top and at the bottom of sensor 16 to the amplifier 3 by way of the electrically conductive traces 74 and 76 which run along the upper and lower strips 62 and 64 between the proximal and terminal end 51 of the ribbon 5.

It is to be understood that the electrically conductive upper trace 74, which runs along the bottom of the upper non-conductive layer 66, may be electrically isolated from the top shielding layer 70 that covers the top of the upper non-conductive layer 66. Likewise, the electrically conductive lower trace 76 which runs along the top of the bottom non-conductive layer 68 of the lower strip 64 of the ribbon 5, may be electrically isolated from the bottom shielding layer 72 that covers the bottom of the bottom non-conductive layer 68. Moreover, the top shielding layer 70 and the bottom shielding layer 72, that cover the top of the upper non-conductive layer 66 and the bottom of the bottom non-conductive layer 68, almost completely surround the ribbon 5 and enclose the electrically conductive traces 74 and 76 thereof as well as the sensor 16 lying therebetween so as to avoid an alteration of the alternating voltage biosignal as could be caused by external electrical and electromagnetic interference.

The adhesive 100 can be attached, at one side thereof, to the outwardly facing bottom of the lower strip 64. The opposite side of the adhesive 100 can be covered by a pull off release film strip 42. When the film strip 42 is pulled off and removed from the adhesive 100, the eye sensor 1 including the ribbon 5 and the sensor 16 that is located, in some embodiments sandwiched, between the upper strip 62 and the lower strip 64 at the proximal end of ribbon 5, can be adhesively attached to the patient's eyelid in such a way to permit the fixation movements of the eyeball of the patient to be sensed, amplified, processed and/or displayed.

By virtue of the ribbon 5 herein disclosed, the sensor 16 can be substantially isolated from mechanical forces that might otherwise be transmitted thereto from the amplifier 3. By way of example, muscular actions, seismic activity and other mechanical motions and vibrations could introduce unwanted artifact noise to the alternating voltage biosignal produced by the sensor 16. To this end, a minimum flexural rigidity depending upon the dimensions and material electricity of the ribbon 5 are preferable in order to avoid the transmission of such mechanical forces to the sensor 16 via ribbon 5.

In some embodiments, the thickness of the ribbon 5 is less than or equal to 25 microns, while the width is about 4-8 mm. In some embodiments, the flexural rigidity of the ribbon 5 is less than or equal to $10 \times 10^{-4}$-in$^4$. As indicated earlier, the ribbon 5 should be provided with slack or strain relief to avoid applying force to the sensor 16. That is the length of the ribbon 5 longer than the straight line distance between the sensor 16 and the amplifier 3. In some embodiments, the length is at least 5% longer than the straight line distance.

Figure 13A:
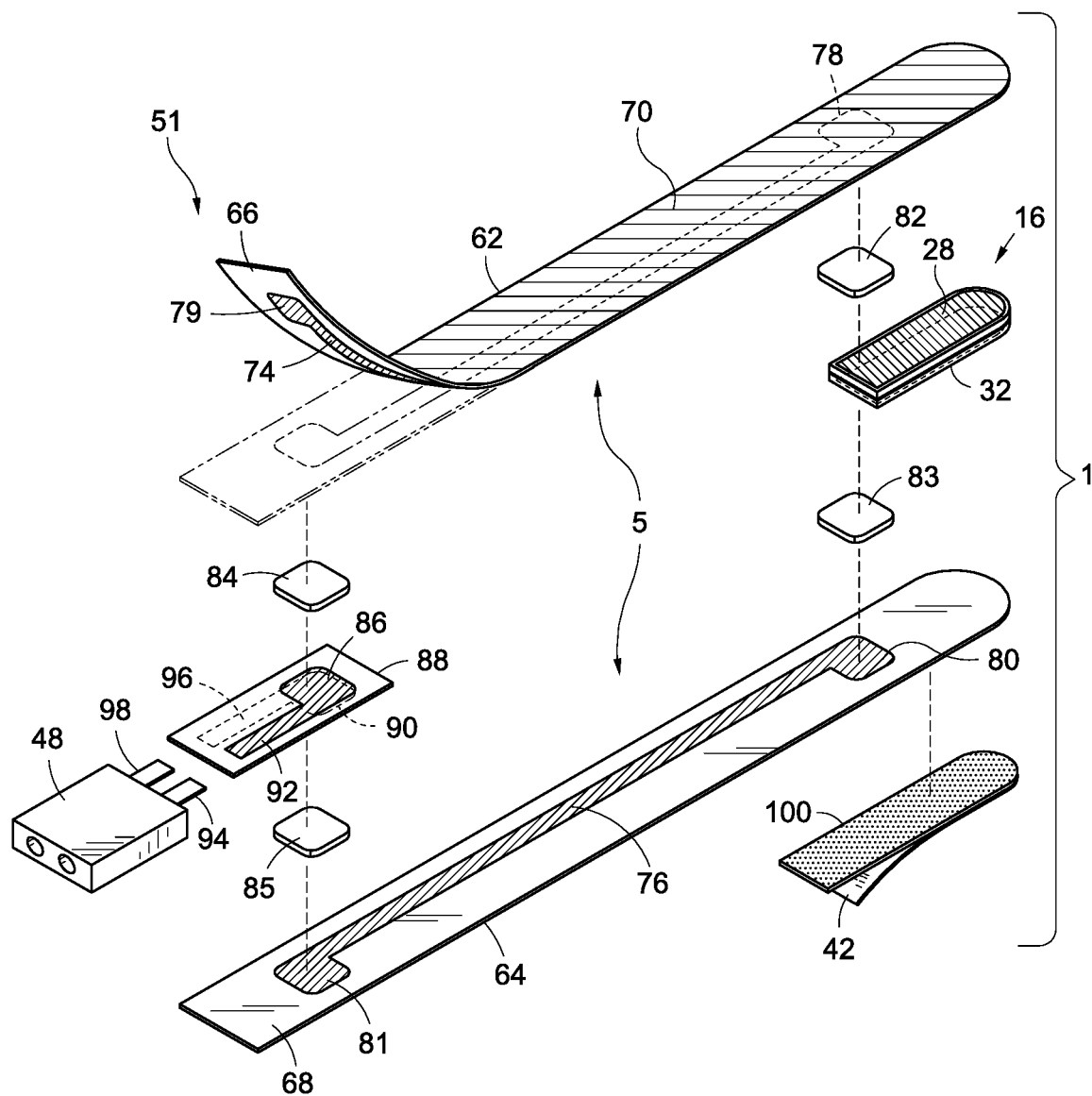
FIG. 13A is an exploded view of an embodiment of a detector comprising a multiple layer piezoelectric element of FIGS. 8-10 is electrically connected to the eye signal amplifier of FIG. 12.
Figure 13B:
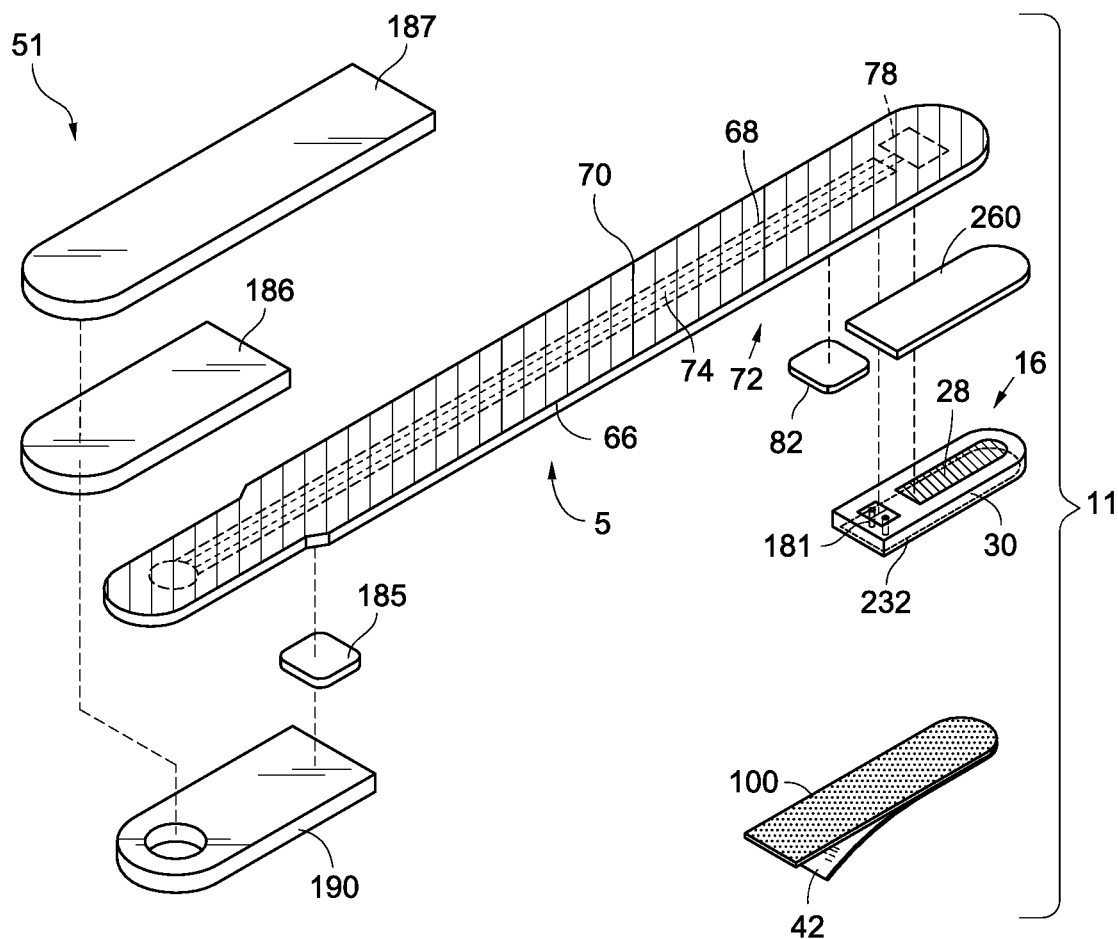
FIG. 13B is an exploded view of an embodiment of a detector.

In FIG. 13B, an embodiment of a detector 11 is shown. The detector 11 comprises terminal end 51, a ribbon 5 and a sensor 16. The terminal end 51 comprises a terminal end backing 187, top shielding pad 186, a bottom shielding pad 185, and an attachment means 190. The sensor 16 comprises a top surface 28 and a bottom surface 232 that are conductive; a sensing element 30; and a bottom conductive surface terminal 180. The bottom conductive surface terminal 180 is electrically coupled to the terminal 78. In some embodiments, the bottom conductive surface terminal 180 and the upper terminal 78 are connected via the conductive upper pad 82. In some embodiments, a portion, if not all, of the sensor 16 is covered by the ribbon 5. In some embodiments, the sensor 16 comprises a bottom conductive surface 232, a conductive bridge 181 that couples the bottom conductive surface 232 with the bottom conductive surface terminal 180.

An embodiment of the ribbon 5, as shown in FIG X, comprises a top shielding layer 70, an upper non-conductive layer 66, a conductive upper trace 74, a bottom non-conductive layer 68, and a bottom shielding layer 72.

Figure 13C:
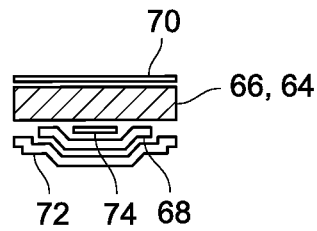
FIG. 13C is cross-section of an embodiment of a ribbon.

In FIG. 13C, an embodiment of a sensor 16 and an embodiment of a ribbon 5 is shown. The ribbon 5 comprises a top shielding 70; an upper non-conductive layer 66; a conductive upper trace 74; a bottom non-conductive layer 68; a conductive upper trace 74; and a bottom shielding 72. The sensor 16 comprises a conductive upper pad 82; a non-conductive layer 260; a top surface 28 and a bottom conductive surface terminal 180 electrically coupled to the conductive upper pad 82; a bottom conductive surface 232 coupled to the sensing element 30. The conductive pad 82, while electrically coupled to the top surface 28 and bottom conductive surface 232, insulates the top surface 28 from bottom conductive surface 232 and individually couples the top surface 28 and bottom conductive surface 232, via the bridge 181, to the conductive upper trace 74 and the bottom shielding layer 72. In some embodiments, the top shielding layer 70 and the upper non-conductive layer 66 of ribbon 5 extend over the sensor 16 so that it is fully covered by a top shielding layer 70 and will be shielded by the top shielding layer 70.

One difference of the embodiment shown in FIG. 13C, as compared to other embodiments of the sensor 16 disclosed, is that bottom shielding layer 72 of the ribbon 5 is able to act as both a trace and electromagnetic shielding for the ribbon 5. This can be an advantage over other ribbons 5 in that there is one less trace or electrical pathway required. This can result in a thinner, more flexible ribbon 5. As mentioned above, the mechanical movement transmitted by the ribbon 5 to the sensor 16 will corrupt readings. Thus, a thinner and/or flexible ribbon 5 will result in more accurate readings. In some embodiments, the bottom shielding layer 72 is grounded by the amplifier 3.

Also shown in in FIG. 13C, an embodiment of the terminal end 51 is shown. The terminal end 51 comprises a top shielding pad 186, coupled to the top shielding layer 70; a bottom shielding pad 185, coupled to the bottom shielding layer 72; and a terminal 191 coupled to the conductive upper trace 74. Some embodiments further comprise an attachment means 190 that is electrically conductive. In some embodiments, the attachment means 190 comprises an electrically conductive magnet. Some embodiments further comprise a terminal end backing 187.

Figure 13D:
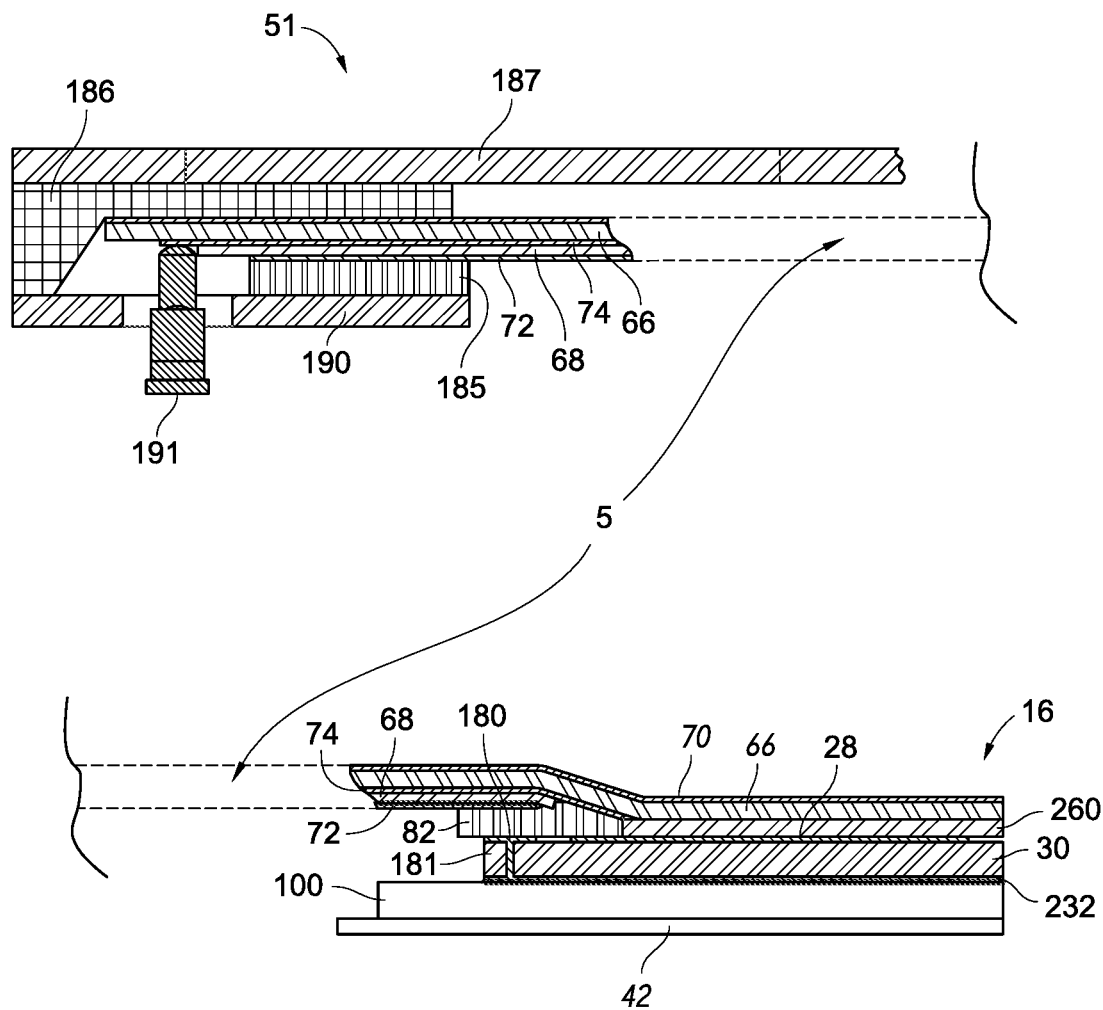
FIG. 13D is a cross-section of an embodiment of a detector and FIG. 13E is a cross-section of an embodiment of an amplifier.
Figure 13E:
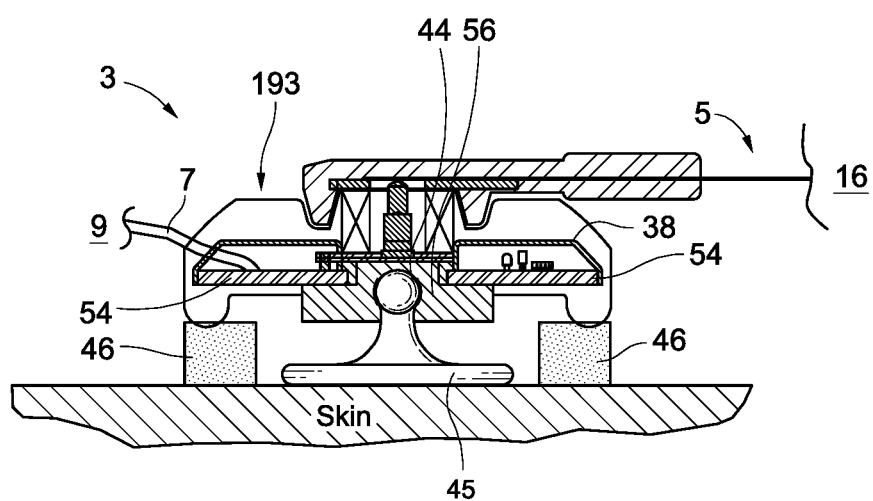

In FIG. 13D, an embodiment of a terminal end and an embodiment of an amplifier 3 are shown. The amplifier 3 comprises an outer housing 193; an electrical receptacle 56; and a printed circuit board 54. Some embodiments further comprise a housing 38. The amplifier 3 can be attached to a grounding electrode 44 that abuts, and grounded to, the patient's skin. In some embodiments, the amplifier 3 comprises the grounding electrode 44 and/or a conductive adhesive patch 46, while in other embodiments, the grounding electrode 44 and/or adhesive patch 46 is provided separately. The aforementioned amplifier grounding electrode 44 is detachably connected to the amplifier 3. The grounding electrode 44 is electrically coupled to the printed circuit board 54 via the electrical receptacle 56, such that the amplifier grounding electrode 44 acts as the ground when attached to the against the patient's skin.

The outer housing 193 will be grounded to the patient via the conductive adhesive patch 46. This effectually serves to ground the shielding of the ribbon 5 and, effectively a side of the sensing element 30, shown as the bottom surface 232. However, it is understood that either side of the sensing element 30 can be grounded by the ribbon shielding. As shown, the top shielding layer 70, at the top of the ribbon 5, is connected to ground at the patient's skin by way of a first electrical path to ground that comprises the top shielding pad 186, the electrically conductive outer housing 193, and the conductive adhesive patch 46. The bottom shielding layer 72 at the bottom of the ribbon 5 is also connected to ground by way of a partially shared path. The bottom shielding layer 72 at the bottom of the ribbon 5 is coupled to the bottom shielding pad 185, and the bottom shielding pad 185 is also coupled to the outer housing 193. Other embodiments further comprise an attachment means 190 to which both the top shielding pad 186 and the bottom shielding pad 185 is coupled to the attachment means, which is also coupled to the outer housing 193. In this same regard, it may be appreciated that top shielding layer 70 and the bottom shielding layer 72 are electrically coupled the outer housing 193.

The printed circuit board is, when attached, electrically coupled to the sensing element 30 via the conductive trace and the terminal 191. The printed circuit board 54 contains conventional signal conditioning and amplifier circuitry by which the fixational eye movement biosignal is alternating voltage biosignal carried by the ribbon 5 is amplified, in some embodiments, by a factor of at least ten. An amplified analog fixational eye movement biosignal is supplied from the amplifier 3 to the signal processor 9 and display 10 of FIG. 17 by means of the shielded cable 7 that extends from the printed circuit board 54 and outwardly through a side of the amplifier housing 38. However, as earlier explained, the fixational eye movement biosignal may also be transmitted from the amplifier 3 to the signal processor 9 over a wireless communication path illustrated in FIG. 18.

Figure 17:
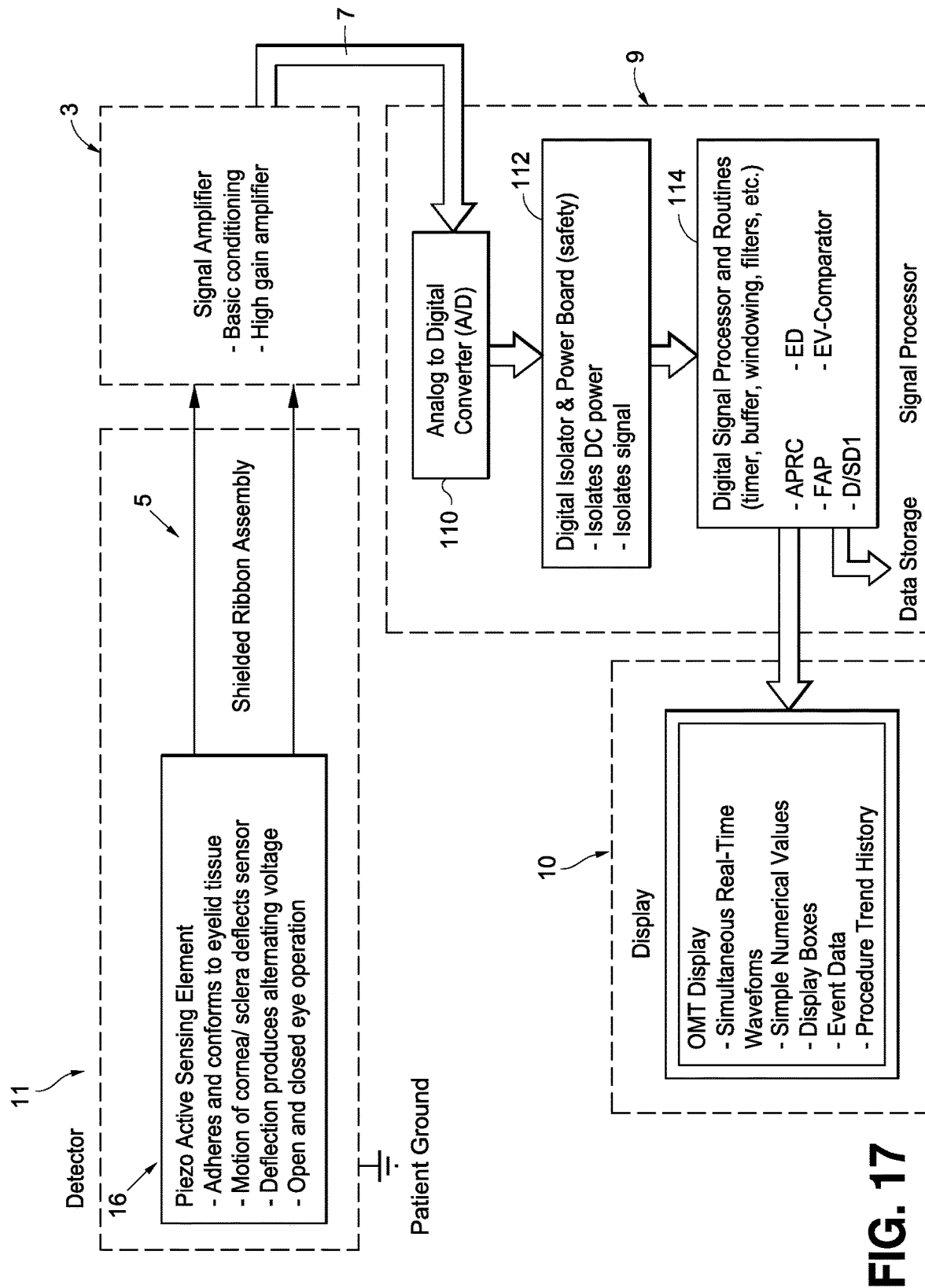
FIG. 17 is a block diagram illustration of an embodiment of a communication system in which the eye sensor of FIG. 2 is coupled to a signal processor and to the display of FIG. 1.

FIG. 17 of the drawings shows an embodiment of the eye sensor 1 connected to the previously mentioned signal processor 9. More particularly, and as previously disclosed, the alternating voltage biosignal generated in response to a deflection of the piezoelectric film 30 (shown in FIGS. 8-13) of the sensor 16 is first supplied to and amplified by the amplifier 3. In one embodiment, the amplifier 3 is capable of filtering the raw fixational eye movement biosignal data and eliminating basic artifacts, such as those caused by head movements and large voluntary eye movements. The signal processor 9 should be capable of clock timing, buffering, windowing and filtering the amplified fixational eye movement biosignal and eliminating the same and other artifacts (such as those caused by undesired eye movements and electrical or electromagnetic interference). The processor and routines 114 are capable of parsing between the different types of fixational eye movements, analyzing individual and combined signal components and computing various parameters such as the dominant high frequency of the OMT component or by computing the combined amplitude and power rate of the MS and OMT eye movements. Further the processor and routines 114 are able to identify events, evaluate events using such amplitude, power and frequency parameters and others in order to compute additional values related to events and trends, such computations often including the use of multiple types of fixational eye movement data. In some embodiments, the eye sensor 1 provides numerical values such as reactivity energy of an event, long term, and short term ratios, before-during- and after event comparative analyses, frequency numbers and displaying the multi-parameter and numerical values results at the display 10. Likewise, a real-time graphical representation of the eye signal waveform (designated 12 in FIG. 1) is also displayed so that a recent history of the patient's brain stem activity and level of consciousness is visually available on the display 10. Further the processor and routines 114 contain stored reference values pertaining to various clinical diagnoses. The processor and routines are capable of comparing data streams in a time-synchronized manner deriving paired combinations of multiple parameters and comparing those computed results against the stored known references in order to support clinical decisions, such as whether to increase decrease or maintain the administration of a drug, or to alert a clinician of an unexpected state of the patient's brainstem and condition.

In some embodiments, the routines 114 comprise frequency and amplitude bandpass filters that are used to provide the information to the monitor on the display 10 (of FIG. 1) which is connected to signal processor 9. By way of example, the amplitude bandpass filters of signal processor 9 are adapted to recognize the input waveform generated by the sensor 16. Any waveform having an amplitude greater than a predetermined threshold (such as that caused by microsaccades) are filtered and eliminated as not being representative of reliable eye information.

A conventional processing technique (e.g., fast Fourier transform analysis, linear predictive modeling or peak counting) is used to compute the frequency of the digital eye biosignal. In a peak counting approach, the fixational eye movement biosignal is sampled during a predetermined time interval. A count of the signal peaks is maintained and incremented during the sampling time. The peak frequency in numerical form (designated 14 in FIG. 1) is displayed on the display 10 (best shown in FIG. 1). Any portion of the fixational eye movement biosignal which is determined to be indicative of gross eye movements and microsaccades is eliminated.

The amplified alternating voltage fixational eye movement biosignal can be supplied from the amplifier 3 to an analog to digital (A/D) converter 110 of the signal processor 9 of FIG. 17 by the shielded cable 7 connected therebetween. The A/D converter 110 converts the analog alternating voltage biosignal to a digital signal to facilitate processing. The digital signal produced by A/D converter 110 is supplied to a digital isolator 112 which isolates the information content of the fixational eye movement biosignal from interference that might be produced by a source of power needed to drive the hardware required to perform the signal processing. The digital isolator 112 also serves an electrical safety purpose of electrically isolating the patient facing portions from the AC main powered portions in the case of an unintended circuit fault.

In some embodiments, the routines 114 comprise frequency and amplitude bandpass filters that are used to provide the information to the monitor on the display 10 (of FIG. 1) which is connected to signal processor 9. By way of example, the amplitude bandpass filters of signal processor 9 are adapted to recognize the input waveform generated by the sensor 16. Any waveform having an amplitude greater than a predetermined threshold (such as that caused by microsaccades) are filtered and eliminated as not being representative of reliable eye information.

A conventional processing technique (e.g., fast Fourier transform analysis, linear predictive modeling or peak counting) is used to compute the frequency of the digital eye biosignal. In a peak counting approach, the fixational eye movement biosignal is sampled during a predetermined time interval. A count of the signal peaks is maintained and incremented during the sampling time. The peak frequency in numerical form (designated 14 in FIG. 1) is displayed on the display 10 (best shown in FIG. 1). Likewise, a real-time graphical representation of the eye signal waveform (designated 12 in FIG. 1) is also displayed so that a recent history of the patient's brain stem activity and level of consciousness is visually available on the display 10.

The processed values frequency of the fixational eye movement biosignal being sampled is tested for validity so that spurious signals can be filtered and eliminated. For example, the frequency of the fixational eye movement biosignal can be inspected and compared with a predetermined frequency range that is known to conform to recognized physiological conditions. What is more, if the patient is subjected to a baseline test prior to being anesthetized, the fixational eye movement biosignal can be compared with the baseline test results. Any portion of the fixational eye movement biosignal which is determined to be indicative of gross eye movements and microsaccades is eliminated.

The amplified alternating voltage fixational eye movement biosignal can be supplied from the amplifier 3 to an analog to digital (A/D) converter 110 of the signal processor 9 of FIG. 17 by the shielded cable 7 connected therebetween. The A/D converter 110 converts the analog alternating voltage biosignal to a digital signal to facilitate processing. The digital signal produced by A/D converter 110 is supplied to a digital isolator 112 which isolates the information content of the fixational eye movement biosignal from interference that might be produced by a source of power needed to drive the hardware required to perform the signal processing. The digital isolator 112 also serves an electrical safety purpose of electrically isolating the patient facing portions from the AC main powered portions in the case of an unintended circuit fault.

The processed values of the fixational eye movement biosignal being sampled are tested for validity so that spurious signals can be filtered and eliminated. For example, the frequency of the fixational eye movement biosignal can be inspected and compared with a predetermined frequency range that is known to conform to recognized physiological conditions. What is more, if the patient is subjected to a baseline test prior to being anesthetized, the fixational eye movement biosignal can be compared with the baseline test results.

Figure 18:
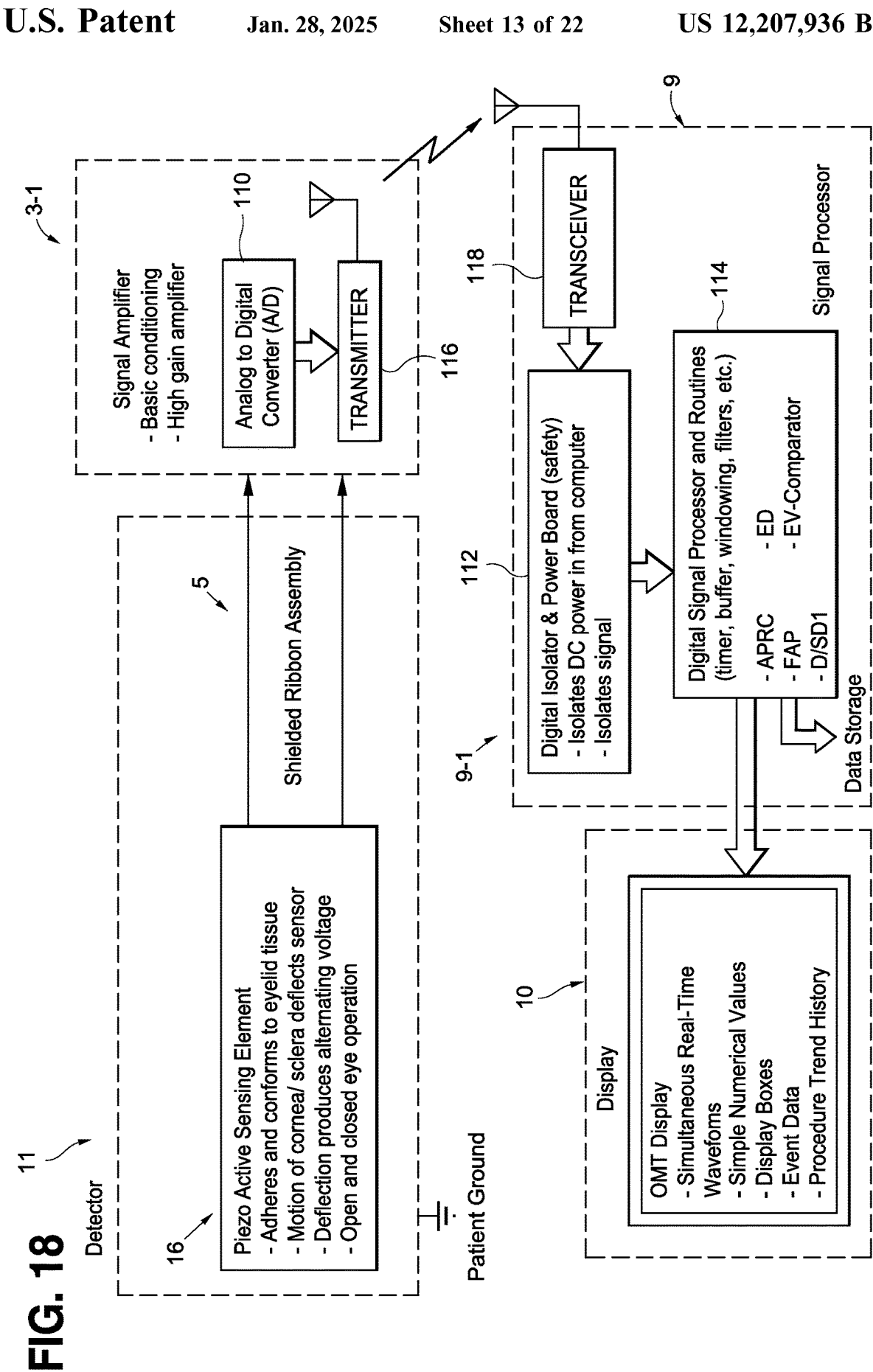
FIG. 18 is a block diagram illustration of an embodiment of a communication system in which the eye sensor of FIG. 7 is coupled to a signal processor and to the display of FIG. 1 over a wireless communication path.

FIG. 18 of the drawings shows an embodiment of the sensor 16 communicating with a signal processor 9-1, which is capable of receiving the amplified analog fixational eye movement biosignal from the amplifier 3-1 over a wireless communication path. In embodiments where the amplifier 3-1 communicates with the signal processor 9-1 over a wireless communication path, the previously described a/d converter 110 is removed from the processor 9 (FIG. 17) and located in the amplifier 3-1 to receive the fixational eye movement biosignal from the ribbon 5. The A/D converter 110 of amplifier 3-1 of FIG. 18 is electrically coupled to a wireless transmitter 116 which is also located in the amplifier 3-1 along with a battery, microcell, or suitable power source, and an antenna. In this case, the shielded cable (designated 7 in FIGS. 7 and 17) is eliminated. Likewise, the signal processor 9-1 of FIG. 18 is provided with a wireless transceiver 118 which is compatible to and capable of communicating with the wireless transmitter 116 of amplifier 3-1. Thus, the signal processor 9-1 may be located remotely from the eye sensor 1 (e.g., at a nurses' station) so that the patient can be monitored as he recovers from an operation or other procedure and returns to consciousness.

Figure 19:
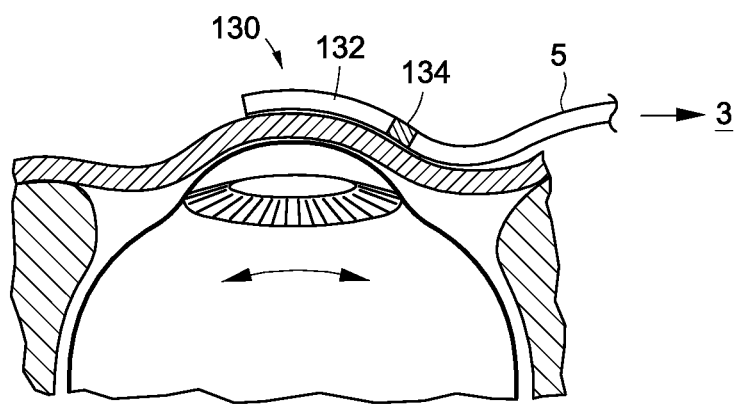
FIG. 19 shows an embodiment for an detector which comprises a mechanical force transmitting arm actuator that is attached to the patient's eyelid at which to be deflected in response to fixational eye movements of the patient's eyeball transmitted thereto so that an electrical biosignal can be generated by a piezoelectric element of the sensor.

It has been disclosed herein that the sensor 16 is attached to the eyelid of the individual being tested such that the sensor 16 is deflected by the fixational eye movements of an individual's eyeball to generate a biosignal. However, rather than having the fixational eye movements applied from the individual's eyeball directly to the sensor 16 to cause a deflection thereof, the fixational eye movements can instead be applied to an intermediate mechanical actuator. FIG. 19 of the drawings shows an embodiment of the detector 130 which comprises a mechanical arm actuator 132 that is attached to the individual's eyelid so as to concentrate forces and stress on a relatively small sensing element 134. In some embodiments, the fixational eye movements are applied from the eyeball to the mechanical arm actuator 132 rather than directly to the sensing element 134.

The mechanical arm actuator 132 of FIG. 19 can be manufactured from a non-conductive medical grade plastic. The mechanical arm actuator 132 is attached to the individual's closed eyelid so as to conform to the shape of the eyelid at which to be deflected in response to the fixational eye movements of the individual's eyeball. The motion sensing element 134 of FIG. 19, which may be identical in construction to the sensing element 30 shown in FIGS. 8-10, is located between the mechanical arm actuator 132 and the ribbon 5. The ribbon 5 may be identical to that previously disclosed when referring to FIG. 13. However, since it is now the lever advantage offered by the mechanical arm actuator 132 of detector 130 which causes the motion sensing element 134 to be deflected, the motion sensing element 134 can be made smaller and require less shielding when compared to the size and shielding. Moreover, the mechanical arm actuator 132 which is not subjected to electrical or electromagnetic interference need not be shielded.

The deflection of the mechanical arm actuator 132 in response to the fixational eye movements of the individual's eyeball through the individual's eyelid below mechanical arm actuator 132 is transmitted to the sensing element 134. The biosignal generated by the motion sensing element 134 is supplied to the amplifier 3 (FIGS. 11 and 12) by way of the ribbon 5 as previously described.

An embodiment of a detector 140 comprises a surface-mounted piezoelectric cable element and for the sensor 142 is described while referring concurrently to FIGS. 20-23 of the drawings. The sensor 142 of detector 140 is a tubular sleeve rather than planar element as in the case of sensor 16 as shown in FIGS. 8-10. More particularly, the sensor 142 is subjected to having its original tubular shape distorted in order to generate a biosignal in response to the fixational eye movements of the individual's eyeball. As shown in the embodiment shown in FIG. 21, the sensor 142 comprises a flexible, electrically conductive interior area 144 which functions as a first electrical terminal. The electrically conductive interior area 144 of arm sensor 142 is surrounded by a flexible intermediate piezoelectric material 146 that is adapted to be compressed and deformed. An electrically conductive exterior surface 148 surrounds the intermediate piezoelectric material 146. The electrically conductive exterior surface 148 of the arm sensor 142 which functions as a second electrical terminal may be surrounded by shielding material (not shown). By way of example only, each of the electrically conductive interior area 144 and exterior surface 148 (e.g., the first and second terminals) of the sensor 142 of the detector 140 can be manufactured from a thin electrically conductive metal mesh.

Figure 21:
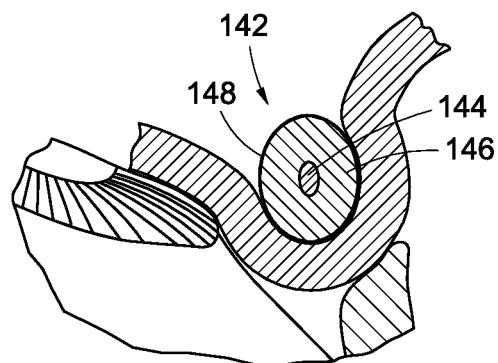
Figure 22:
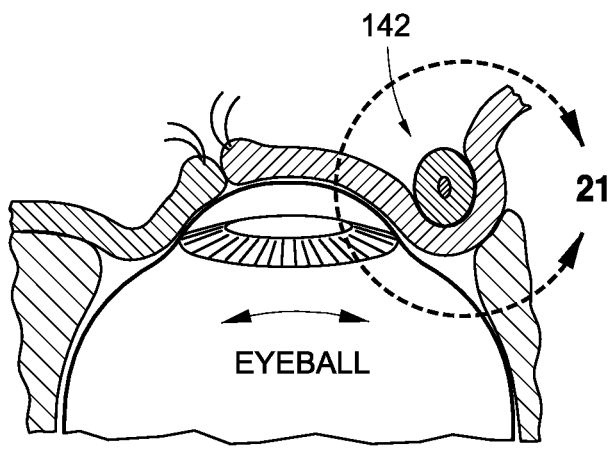

The tubular surface-mounted piezoelectric sensor 142 of the detector 140 can be located in the folds of the individual's eyelid where it will be responsive to the fixational eye movements of the individual's eyeball transmitted through the eyelid so as to undergo a compression and a deformation by which to generate a corresponding voltage. With the sensor 142 initially in a relaxed state, the electrically conductive interior area 144 and an exterior surface 148 as well as the intermediate piezoelectric material 146 lying therebetween all have a cylindrical configuration (not shown). However, when the tubular sensor 142 receives a compressive force in response to fixational eye movements of the individual's eyeball, the shape of each of the electrically conductive interior area 144, exterior surface 148 and intermediate piezoelectric material 146 is distorted and thereby assumes an elliptical configuration as shown in FIGS. 21 and 22.

The distortion and change of shape of the intermediate piezoelectric material 146 produces a biosignal between the first and second terminals (e.g., the electrically conductive interior area 144 and the electrically conductive exterior surface 148) of the surface-mounted piezoelectric element sensor 142. The biosignal generated by the arm sensor 142 of the detector 140 is supplied to the amplifier 3 by way of a tubular-to-planar strain relief adapter 150 (of FIG. 20) of the detector 140.

Figure 20:
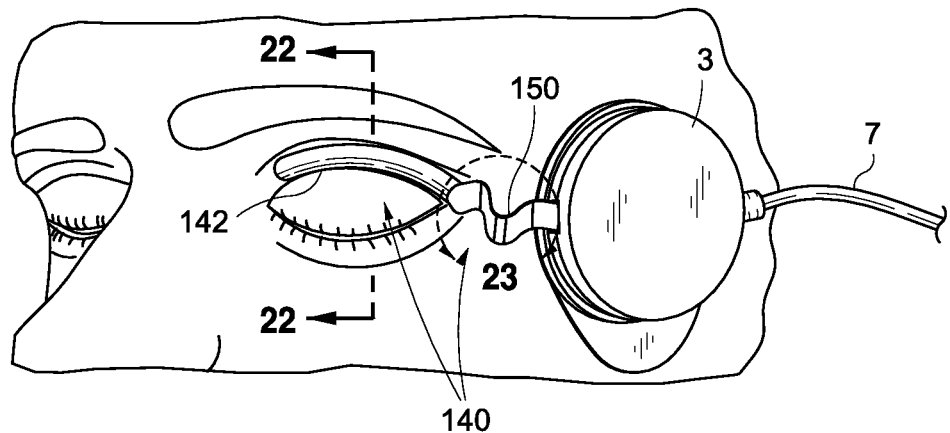
FIGS. 20-22 show a different embodiment for an ocular microtremor (eye) sensor having a tubular surface-mounted detector that is located within the folds of the patient's eyelid at which to undergo a shape distortion in response to fixational eye movements of the patient's eyeball transmitted thereto for generating an electrical biosignal.
Figure 23:
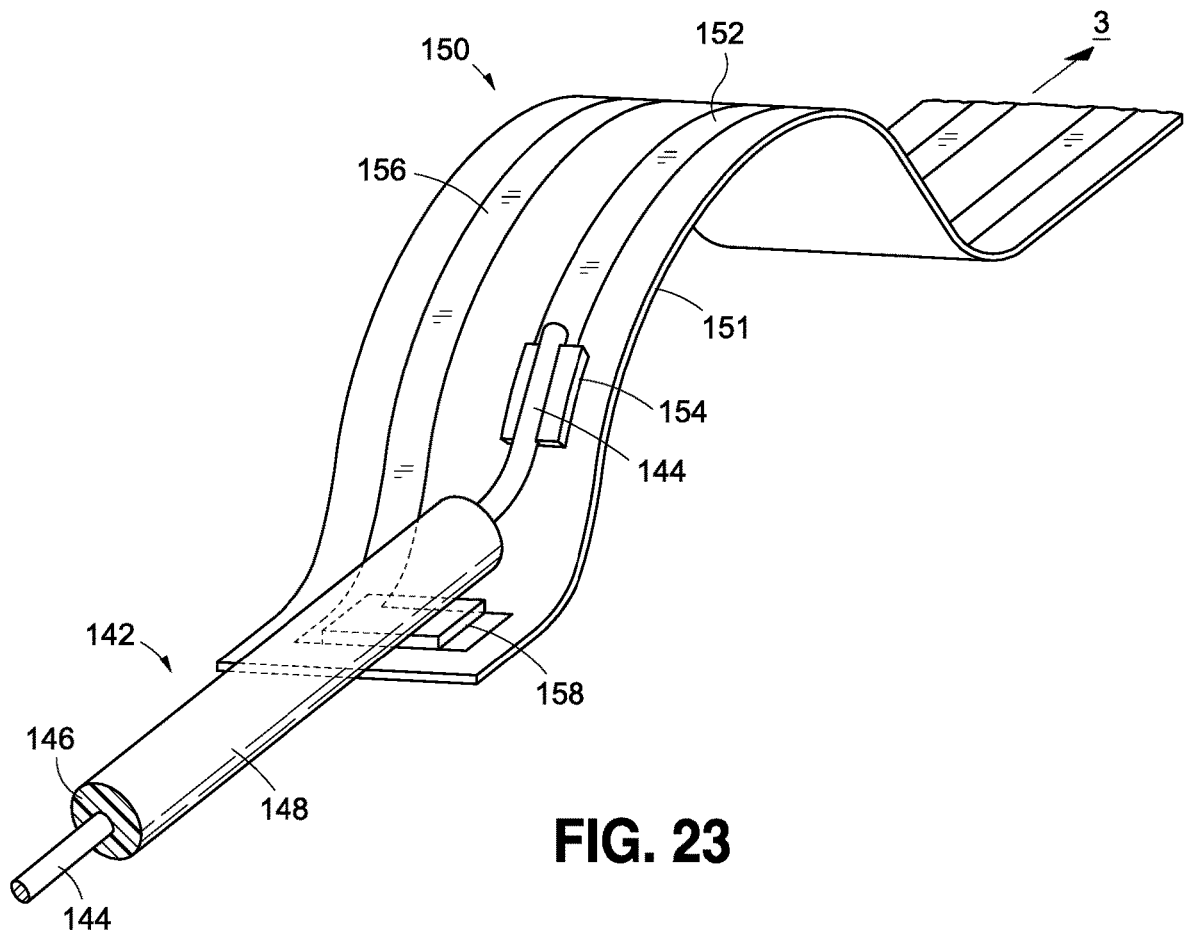
FIG. 23 is an enlarged detail of a tubular-to-planar strain relief adapter taken from the detector shown in FIG. 20.

Referring specifically to an embodiment shown in FIG. 23, details of the tubular-to-planar strain relief adapter 150 of the detector 140 of FIG. 20 are shown by which the electrically conductive interior area 144 and the electrically conductive exterior surface 148 of the sensor 142 are connected to the printed circuit board 54 (FIG. 12) of amplifier 3 in substitution of the ribbon 5. The strain relief adapter 150 comprises a flexible substrate 151 manufactured from a non-conductive material and having an arcuate (e.g., curved) configuration. The curved substrate 151 is adapted to be flexed in response to mechanical forces applied thereto to absorb pulling forces that could otherwise be applied to the sensor 142. A first electrically conductive trace 152 runs longitudinally along the substrate 151 from an electrically conductive first contact pad 154 to the amplifier 3. An electrically conductive second trace 156 runs longitudinally along the substrate 151 from an electrically conductive second contact pad 158 to the amplifier 3. The first and second electrically conductive traces 152 and 156 are arranged in spaced side-by-side parallel alignment along the substrate 151 of strain relief adapter 150 so as to be electrically isolated from one another.

The electrically conductive interior area 144 is connected (e.g., pushed into locking engagement) at an attachment (e.g. a groove formed in the first contact pad 154) on substrate 151. The second contact pad 158 extends laterally across the substrate 151 so as to lie in front of and in axial alignment with the first contact pad 154. Therefore, at the same time that the conductive inner area 144 of the sensor 142 contacts the first contact pad 154, the electrically conductive exterior surface (e.g., the second terminal) 148 of the tubular sensor 142 will be automatically aligned to lie on and contact the second contact pad 158. Accordingly, when the tubular sensor 142 undergoes a distortion and a change of its shape in response to fixational eye movements of the individual's eyeball, the corresponding biosignal generated by the arm sensor 142 between the electrically conductive interior area 144 and electrically conductive exterior surface 148 thereof is transmitted for amplification to the amplifier 3 by way of respective ones of the first and second conductive traces 152 and 156 of the strain relief adapter 150 which run along the substrate 151.

Figure 24:
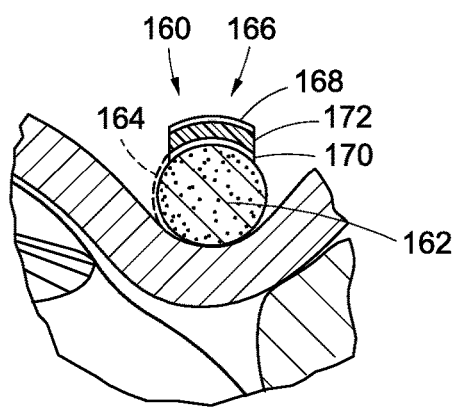
FIG. 24 shows yet another embodiment for an ocular microtremor (eye) sensor having a cylindrical force transmitting actuator that is located within the folds of the patient's eyelid at which to undergo a shape distortion in response to fixational eye movements of the patient's eyeball transmitted thereto so that an electrical biosignal can be generated by a piezo-active sensing element of the detector.

FIG. 24 shows an embodiment of a detector 160 comprising a mechanical actuator and a piezo-active sensing element. Like the detector 130, that was described while referring to FIG. 19, the detector 160 of FIG. 24 comprises a mechanical force transmitting actuator that is responsive to the fixational eye movements of the individual's eyeball. In this case, however, rather than an arm actuator attached to the individual's closed eyelid, a cylindrical force transmitting actuator 162 is located within the folds of the eyelid to lie closer to the eyeball than the piezo-active sensing element.

The cylindrical force transmitting actuator 162 of detector 160 is adapted to be compressed and undergo a deformation in response to the fixational eye movements of the individual's eyeball transmitted through the individual's eyelid. The cylindrical force transmitting actuator 162 can be manufactured from a compressible material, such as a medical grade foam rubber, or the like. By way of a second example, the cylindrical force transmitting actuator 162 is filled with a compressible liquid, such as a gel, or the like. In the event that the cylindrical force transmitting actuator 162 is filled with liquid, the actuator is preferably surrounded by a flexible envelope 164 (shown in broken lines in FIG. 24).

The detector 160 comprises a sensor 166 that is generally planar so as to be adhesively attached over and conform to the shape of the cylindrical force transmitting actuator 162. The sensor 166, which can be a piezo-active sensing element, may be identical to the sensor 16 that was previously described while referring to FIGS. 8-10. However, to reduce the size of the detector 160, the sensor 166 embodiment that is shown in FIG. 24 comprises an upper electrically conductive surface 168 which functions as a first terminal and a lower electrically conductive surface 170 which functions as a second electrical terminal. An intermediate piezoelectric material portion 172 is located between the upper and lower electrically upper electrically conductive surface 168 and lower electrically conductive surface 170.

The fixational eye movements of the individual's eyeball are applied through the individual's eyelid and result in a deformation and a change of shape of the cylindrical force transmitting actuator 162. The deformations of the cylindrical force transmitting actuator 162 are transmitted to the sensor 166 which lies over and against the force transmitting actuator 162. Accordingly, the intermediate piezoelectric material portion 172 of the sensor 166 is correspondingly deflected so that a biosignal is produced between the first and second terminals (e.g., the upper and lower electrically conductive surfaces 168 and 170) lying on opposite sides of the intermediate piezoelectric material portion 172. The biosignal may then be supplied to an amplifier (like that designated 3 in FIGS. 11 and 12) by way of a flexible (like that designated 5 in FIG. 13).

The electrically active sensing element for the eye sensor 1 has been described as typically being a sensor 16 that is configured to generate a voltage in response to the sensing element being deflected by the fixational eye movements of the patient's eyeball. However, any of the sensors (e.g. 16, 166, 142) disclosed herein may comprise, and any of the sensing elements (e.g. 30) disclosed herein may be, other types of electrically active devices, such as a variable resistance element (e.g., a strain gauge), a variable capacitor, accelerometer or a variable inductor just as long as the outputs of which will be indicative of the fixational eye movements of the eyeball of the individual undergoing testing.

Figure 26:
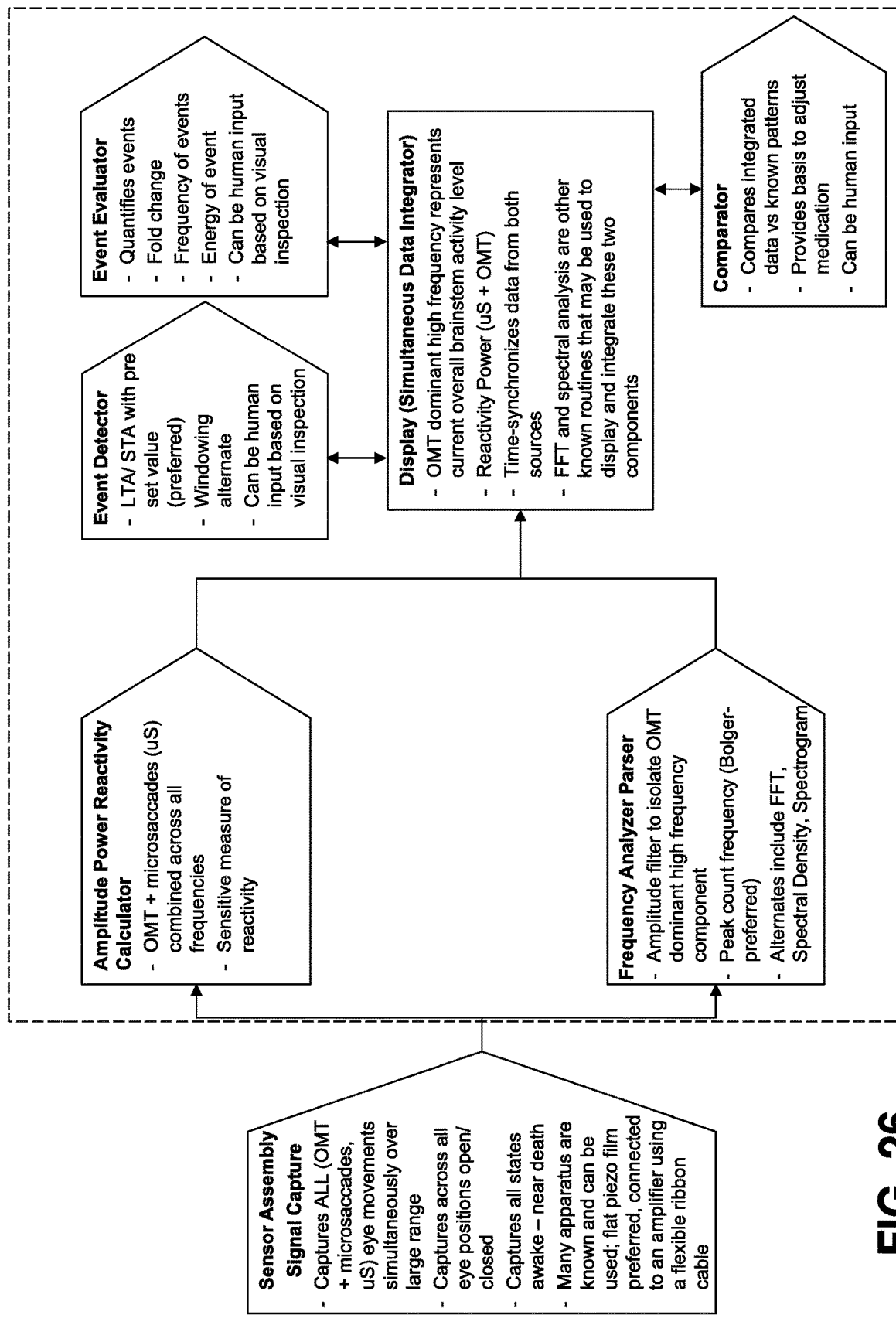
FIG. 26 shows an embodiment for a routine to process eye movement data.

Referring now to FIG. 26 where an embodiment of the processor and routines 114 is shown. The fixational eye movement data is obtained by the sensor, amplified and converted into valuable information through the use of the processor and a pair of first and second routines designed to derive certain components and generate two separate parameters. A third routine is used to integrate and synchronize the data streams so that joint values may be considered and analyzed simultaneously so as to provide better more accurate views of the state of the patient's brainstem and condition. The paired or joint values often provide superior benefit than either of the individual or component values. Fourth and fifth event detection and evaluation routines interact dynamically with the third integrating and synchronizing routine so as to be able to establish time windows relating to certain events and patterns. Examples include surgical stimuli, other endogenous or exogenous stimuli, trend-based shifts in values, procedural events, snoring patterns, sleep, and drug-related events and the like. It is found that certain analyses such as the reactivity energy of an event, or the long term average of a parameter before and after an event, relating to and requiring the identification and evaluation of these events are quite important indicators of patient conditions, past, current or predicted. An embodiment may provide an early display of parameters so as to allow clinicians to visualize and interpret data, may display data further in the processing routines so as to present individual numerical values and or real time streaming parameters. It is also expressly understood that pre-determined set points and user input values may be combined to produce the desired results.

In some embodiments, the fixational eye movement data comprises of OMT and MS. The fixational eye movement data can be continuously obtained from a subject via the detector, amplified in a first stage, filtered with an analog filter to remove low-frequency noise components below 5 Hz, then further amplified to achieve an overall amplification in the range of 2000 to 2500 gain. After converting the amplified analog signal to a digital signal with the use of 16-bit low noise converter and 1000 cps acquisition rate. The fixational eye movement data is processed by an amplitude power calculator (APC) and a frequency analyzer parser (FAP). Both of the APC and FAP employ a set of conditioning and filtering routines that can be set to a variety of values and present either common or differing resultant filtered data streams to each or one or the other of the APC and FAR. The result data streams may be comprised of isolated eye movement components or combined components as joint signals or joint signal data. The derived and generated individual components, joint signals and parameters and combinations are selected to provide the most accurate and beneficial perspectives on the brainstem activity.

The filters can employ a bandpass filter, notch, and amplitude filter to filter out data of frequency and amplitude components with values above and below and even within those values known for OMT and MS jointly. Notch filters can be used to filter out specific known artifacts such as that of AC mains or other known unwanted interferences. Additionally, a variety of known filtering and signal processing techniques are known and may be employed such as wavelet denoising, frequency band grouping and the like.

The aforementioned features of the eye sensor such as conforming application to the noise-deadening eyelid tissue, shielding, flexible ribbon mechanical vibration separation, grounding, and the like can operate together with the conditioning and filtering routines ensure that only eye movement signal data is presented. In an embodiment, the joint signal resulting comprises the data represented by the two OMT and MS fixational eye movement components and only the data represented by the two movements contained within the biosignal generated by the eye and received by the sensor.

The APC employs a pre-set data window, buffers the voltage vs. time data for that window and conducts an initial bandpass frequency filtering routine set between in a manner that, when accounting for digital filter rolloffs and resonances, allows the full range of low-frequency MS and high-frequency OMT fixational eye movement data to be presented. While the overall average frequency of the MS is known to be in a range between below 1 hertz to 5 hertz, it is the observation of the applicant that the MS bursts combined with resonance of the eyeball tend to increase the effectively measured frequency value of the MS to a range between 5 to 25 hertz, often 13 to 22 hertz. The APC computes the two-second average power or total eye power using the frequency filtered conditioned joint signal comprising both OMT and MS components. First, the conditioned filtered voltage values generated by the sensor at a rate of 1000 cps are converted to their absolute values and then summed over a time windowing period, such as two seconds. The resultant power value represents the work accomplished by the eye over the time period. It is discovered that this power value reflects a significant portion of the power of the fixational movement as derived from the OMT and MS amplitudes and is a sensitive measurement of the brainstem reaction to stimuli. The parameter is especially useful in depressed conditions where a patient demonstrates no observable physiological responses or reactions to intentional or other stimuli, effectively assessed to be "non-responsive." However, it is discovered that when the combined total eye power parameter is employed, that actually below visible or observationally-detectable levels a brainstem response is present and can be illustrated on the display. In addition, data suggests that not only can the system "see the useable" but that the resultant signal or joint signals can be used to determine a proportionality or relative value of the response. A further feature of the system calls upon the event detection and evaluator routines so as to calculate the total energy of the response or the reactivity energy. This calculation, comparison of the calculated value beneficial employment of the proportionality characteristic is described later.

In The FAP runs in tandem with the APC. Whereas in a different regime, the FAP operates predominantly in the frequency regime whereas it can be seen that the APC operates predominantly in the amplitude regime, the FAP operates predominantly in the frequency regime. The FAP comprises a pre-conditioning and filtering routine of the general description provided with that of the APC. In one embodiment the initial eye sensor system working together with the initial frequency filtering results in the same filtered data stream as is presented in the APC and described above. However, the FPC runs additional filtering steps so as to isolate only the OMT component of the signal. Dual amplitude filters are employed. One filters out the low end noise component associated with the electronic circuits. While immaterial in the case of the APC and amplitude regime, low end noise interferes in the frequency regime and must be removed. A second an amplitude filter that is capable of isolating the dominant high-frequency component and/or the peak count frequency of the OMT.

One signal processor 9 which is suitable to be connected to the amplifier 3 to receive the amplified biosignal and perform the aforementioned processor functions is shown and described in U.S. Pat. No. 7,011,410 issued Mar. 14, 2006, the details of which are incorporated herein by reference. Therefore, only a brief description of the signal processor 9 will be provided below.

A conventional processing technique (e.g., fast Fourier transform analysis, linear predictive modeling or peak counting) is used to compute the frequency of the digital eye biosignal. In a peak counting approach, the fixational eye movement biosignal is sampled during a predetermined time interval. A count of the signal peaks is maintained and incremented during the sampling time. The peak frequency in numerical form (designated 14 in FIG. 1) is displayed by the display 10 (best shown in FIG. 1). Any portion of the fixational eye movement biosignal which is determined to be indicative of gross eye movements and microsaccades is eliminated in this case. The frequency parser is able in this manner to compute what is known as the dominant high frequency component of the fixational eye movement signal as is known to be represented by the highest frequency OMT component.

OMT frequency is an excellent indicator of the current continuous level of brainstem activity. It drops rapidly upon propofol administration or the loss of consciousness. It is indiscriminatory in the sense that any means of attenuating the brainstem activity lowers the peak count frequency—a combination of different drugs, sleep states, drowsiness, injury and the like described by Bolger. Conversely, lightening of drug concentration, awakenings, and stimuli serve to raise the OMT frequency values. As such OMT frequency provides unique insights as to the state of the patient, but it is hereto disclosed that certain clinical diagnoses are improved when the isolated OMT peak frequency is considered in a time synchronized manner about certain events in conjunction with the total eye power parameters delivered by the APC. The FPC thereby delivers a continuous data stream.

In some embodiments, a display 10 comprises a simultaneous data integrator (SDI) that can integrate each of the results of the APRC, FAP, event detector (ED), and/or the event evaluator (EV). In some embodiments, the two or more of results of the APRC, FAP, event detector, and/or the event evaluator can be combined into a combination result. The presentation of one or more of the results, can be shown with one or more on the same screen, alternating screen of the same display unit, and/or on different screens. The presentation can take the form of a track line, FTT, a spectral analysis, a quantitative number, multiple track lines and/or combination track lines. The presentation can be shown so that the time is synchronized for all the items presented. Additional methods of computing and displaying combined parameters of frequency and amplitude have been used effectively. For example what is commonly known as a spectrogram displays colored toned images that represent synchronized time information, frequency and amplitude data. In the case of surgeries, such techniques receiving the conditioned filtered eye signal data provide effective means of illustrating events, trends and changes to the patient's brainstem and sedation or anesthetic state.

Some embodiments comprise an event detector. The event detector can register an LTA and/or an STA. The event detector, in some embodiments, include a predetermined value or multiple for which the STA exceeds the STA so as to register an event. Tertiary clinical input methods can also be used.

Some embodiments include an event evaluator that can quantify the events. This quantification can be based upon previously obtained data that can be stored locally, in the cloud and or the Internet. The event evaluator has the ability to analyze fold changes, frequency of events, and/or energy of the event(s) in quantifying the events.

In some embodiments, the APRC and FAP is used to present a displayed results for a user.

In some embodiments, a comparator compares the fixational eye movement data and/or the results to known data patterns. The comparison can be presented on the display. The comparator can output alarms, instruction, and/or cause an action by an automated system. For example, the comparator may compare the current data points to known data points. If the comparator determines that a negative situation has arrived, or notices something that may be a forbearer of, it can instruct the display 10 to present an alarm and/or suggested instruction. In other embodiments, the comparator can autonomously alter drugs being supplied to the patient.

Some embodiments comprise an eye sensor 1, to measure the amplitude of the fixational eye movements, specifically microsaccades together with ocular microtremors, and a processor 9, having pre-programmed routines to isolate certain components, manipulate and recombine data and present results. The ARPC performs a power calculator method and the FAR runs a frequency analyzer method to simultaneously produce two data streams. In some embodiments, the data streams are the amplitude of the fixational eye movement and a frequency component of the OMT. Each of the two data streams can provide raw or computed values of each of power and frequency parameters, and the data streams represent distinct but interrelated parameters of the eye movement signal and therefore distinct but interrelated parameters of brainstem activity. In some embodiments, the comparator performs a method that comprises matching brainstem activity patterns with closest known reference pattern and may respond according to pre-programmed rules.

In some embodiments the SDI runs a simultaneous calculation method. The data integrator interacts with a fifth routine; event evaluator that employs event data and analysis window from the event detector to convert power data into reactivity data and presents integrated paired combinations of reactivity and frequency parameters, collectively representing brainstem activity patterns.

The combined simultaneous measurement and analysis of the individual and two types of fixational eye movements and interpretation of combined patterns provides new and useful insights and enables the parsing between heretofore indistinguishable conditions and new diagnoses. Many workers have used MS fixational movements to measure attentional response, determine states and to diagnose neurological conditions. This work centers on those conditions where MS play an important role in visual perception and visual acuity. As such, the study of MS is limited predominantly to measurement systems used with healthy awake subjects with open eyes, or in ways that connect to vision processes. It is important to note that MS have different characteristics than OMT, which make each more suitable for some tasks and less so for others. For example MS motions measured directly from the eyeball on awake subjects are easier to measure with general purpose instruments of resolution limited to the micron range and instruments tuned for that specific size range. OMT on the other hand is a nanometer level amplitude, about 40 times smaller in amplitude than MS, and requires high sensitivity sensors, hi-gain amplifiers, and precautionary elements to eliminate or reduce noise artifacts, more so that general instruments. The MS are so large comparatively, that they render measurements OMT inaccurate unless the large waves are removed via filtering or other known means. Conventional OMT sensor systems are tuned for that range of motion as required for systems dedicated to measuring nanometer to 1 micron level movements and are primarily focused on the frequency, not the amplitude of the OMT. Also given that OMT is measured predominantly with frequency units of values higher than those known for MS, prior art teaches one to avoid including microsaccadic low-frequency counts to avoid inaccurately biasing the higher counts from OMT. Thus, according to the prior art and the purposes thereof, the MS provides no useful information and should be filtered out in order to isolate the amplitude of OMT.

Figure 27A:
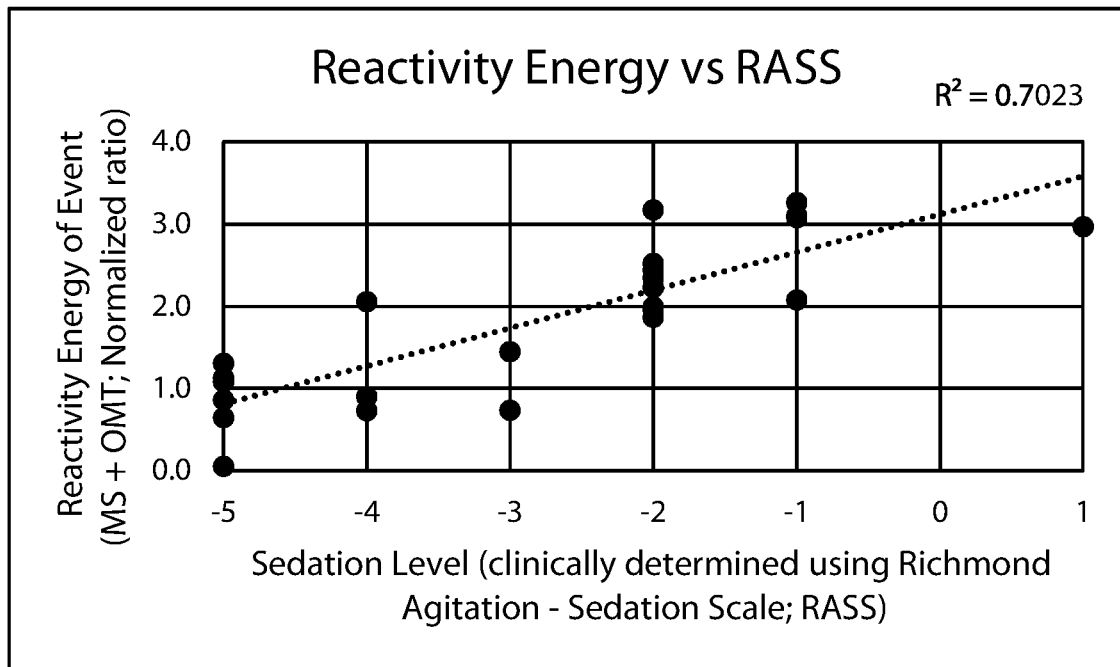
FIGS. 27A, 27B, and 27C show an example of data from 13 different test subjects on different brainstem activity routines.
Figure 27B:
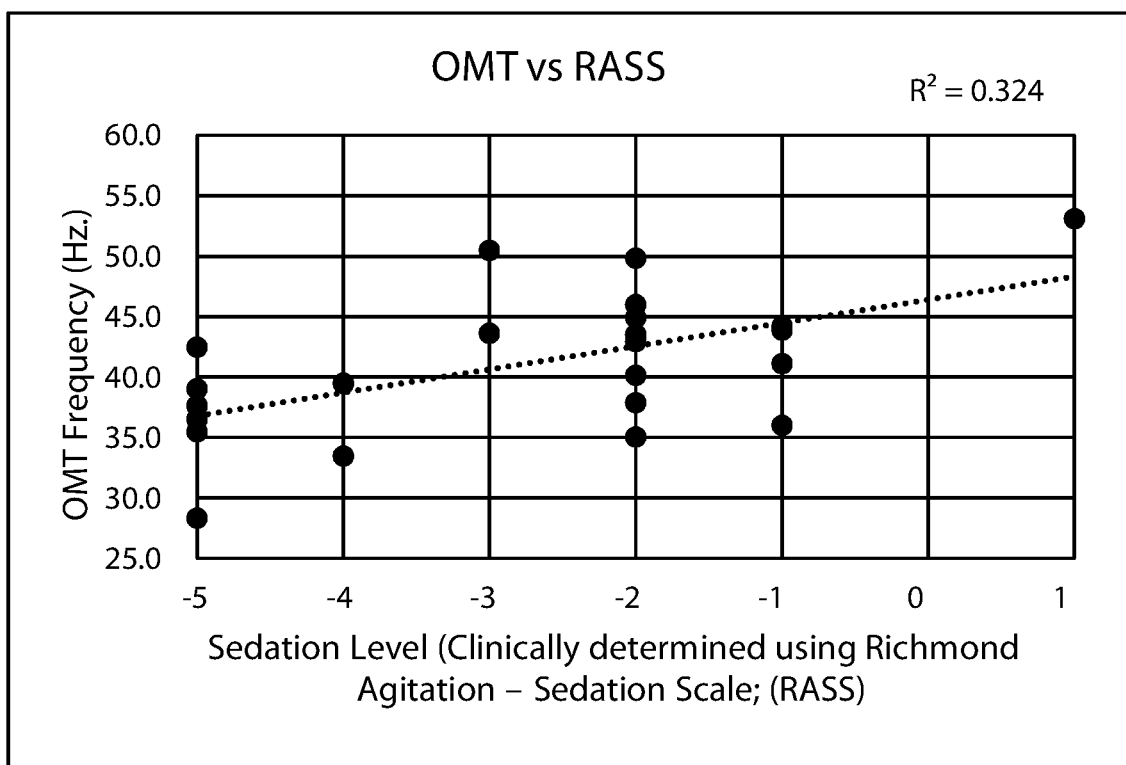
Figure 27C:
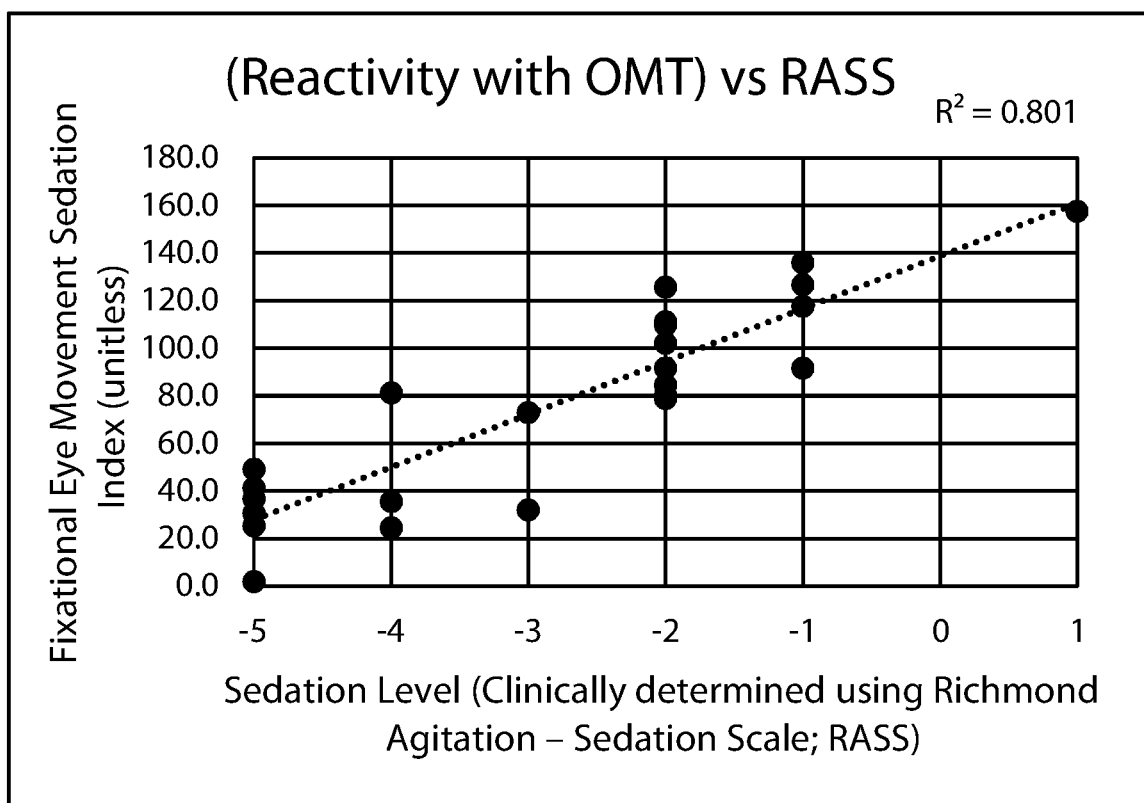

FIGS. 27A-27C demonstrate one example of an embodiment in use is wherein the combined use of two fixational eye movement and associated parameters can yield superior diagnoses than can the use of either of the components alone is managing the proper administration of sedatives for critically ill patients in the intensive care unit (ICU). The results of significant experimental piloting by sifting through a vast variety of potential parameters and variants of fixational eye movements and the statistical results of a controlled clinical study are depicted in FIGS. 27A-27C. This study was designed to demonstrate the validity and reliability of ocular microtremor "OMT" during anesthesia and intensive care sedation. The primary endpoint was the correlation between OMT data and the current standard of care; a proven valid and reliable subjective physiological assessment instrument called the Richmond Agitation Sedation Scale (RASS). Hence the applicant sought to demonstrate a statistically significant correlation between OMT values and the RASS standard that was administered as a controlled form of stimulus according to an approved research protocol.

Turning now FIG. 27B it is reported that the first correlation between the traditional OMT signal frequency peak count alone and the RASS standard where the R2 value is 28% The correlation statistics are significant but the range of scores is high.

The applicant hypothesized that RASS is a measure of patient reactivity and developed a frequency-independent measure of reactivity based on the microsaccade component of fixational eye movements. The MS component of the biosignal had been omnipresent in the raw eye movement data, but the prior art taught to eliminate the MS component, by way of strong frequency and amplitude filtering. The new parameter employs the processor and routines best shown in FIG. 26 so as to compute the reactivity energy of a stimulus event. The SDI receives the total eye power data from the APC, incorporates event information from the ED and EV and computes a normalized energy value. The LTA of the total eye power up to the event is calculated and added together over a designated time window leading up to the event and results in the pre-event energy. The eye energy corresponding to the event is calculated by summing the power values over a same designated time period during the event. The change in energy from the pre and during periods are determined by subtracting the pre-from the during value to result in the change in energy due to the event. This change can be divided by the incoming LTA of the energy or suitable value so as to normalize across patient variations. The log 10 of this normalized change in energy is an example of a useful and accurate event evaluation. This parameter embodiment, reactivity energy of event, is shown on the left axis of FIG. 27A Applicant conducted secondary analysis incorporating the new measure of reactivity. Again, in FIG. 27A it can be seen readily by the trained eye that the correlation statistics are R2 value is 70%—known to be significant, but there remains a wide range of scores. Finally it was realized that both measures together provide a superior result than either of the two parameters individually. FIG. 27C shows the correlation statistics when both parameters are used together. In this case, when parameters are combined the correlation statistics r2 value increased by 10% to over 80% which is determined to be an excellent correlation and the basis for new clinical practices. In this case, the OMT frequency was multiplied with the reactivity energy of event parameter to produce a new unitless index named fixational eye movement sedation index and shown on the left axis of the graph in FIG. 27C. It can now be seen that one can adapt this technique with the use of the comparator to resolve a long standing problem of mismanagement of medication in the ICU. Current values for the patient can be computed using the methods and apparatus described herein and they can be compared against the present correlational references now known in the form of a database. Comparisons can yield directions to drug administration. Should the index value exceed a target level, then the drug is increased. Conversely, should the measured index value be below the target level, then the drug rate should be lowered or discontinued altogether until the patient achieves the desired state. In the case where the index value matches the target value, then the drug level is maintained as it is.

Subsequently it has become clear that one of the reasons for the above described discrepancy is that the use of OMT peak frequency alone does not discriminate well between the conditions of sleep-induced brainstem depression and that depression state caused by drug depressions. Drug depressions are more forceful in maintaining brainstem depression than are sleep-induced mechanisms. The applicant has measured patient OMT values for deeply sleeping naturally subjects to be in the same low frequency range as for patients who are highly anesthtized with powerful drugs. However, importantly, the sleeping patient is arousable with a stimulus of the same approximate strength than that given to an anesthetized patient who does not even respond let alone become aroused. Drugs attenuate the brainstem more forcefully than do natural sleep mechanisms. In a similar manner the reactivity energy and power derived from the MS component tends to be less discerning in more awake zones where the relative increases in MS amplitudes are less if not pronounced as if they are already "full on" and so that additional provocation stimuli do not dramatically further enhance the amplitude. The OMT frequency however is an excellent measure of activity at awake levels and fully proportional to changes at that level. Hence again, the explanation for why the combination of signal parameters is of greater value and used for new unexpected purposes than are either of the individual values alone. This combinatorial value becomes especially pronounced when for the first time multiple fixational eye movement data is taken together and employed across the full range of arousal scale from near death as in deep anesthesia or coma through to wide awake and even aroused above normal states. This is the reason that the addition of the reactivity parameter derived from the MS component considered in concert with the OMT value enhances overall statistical diagnostic performance.

Consistent with the embodiments of the present invention and the disclosed ICU sedation example, an embodiment includes a simple decision matrix that allows the comparator to easily identify one of three sedation states being deep, moderate and light. Values of OMT frequency below a certain threshold around 43 hertz, accompanied by low reactivity values below 1.5 indicate together a deep state. OMT values above 43 hertz accompanied by reactivity values greater than 2.5 indicate a light state. Frequency values below 43 but accompanied by high reactivity between 1.5 and 2.5 are most consistent with a light state. Intermediate values of reactivity between 1.5 and 2.5 coupled in time synchronized fashion with OMT frequencies below 43 hertz are most consistent with a moderate state, and so forth.

Similarly consistent with the current invention, circadian rhythms and sleep states can be illustrated for ICU patients and the sleep state may be parsed from the drug induced swedation state so as to facilitate the accumulation of proper rest or to enable the earlier diagnosis of prevalent co-morbid conditions such as delirium.

Sleep analysis using embodiments of the present invention is not limited to to ICU sedated patients. In some embodiments the invention is capable of identifying respiratory-related events during sleep that are used in the diagnosis of sleep related disorders. In yet some embodiments, the amplifier 3 is reduced in size so as to match the smaller anatomy of a neonatal late premature infant used to detect apnea of prematurity and to map the trend of brainstem development during a stay in the NICU and after discharge for periods long enough for the patient to achieve full mature brainstem development.

Figure 28:
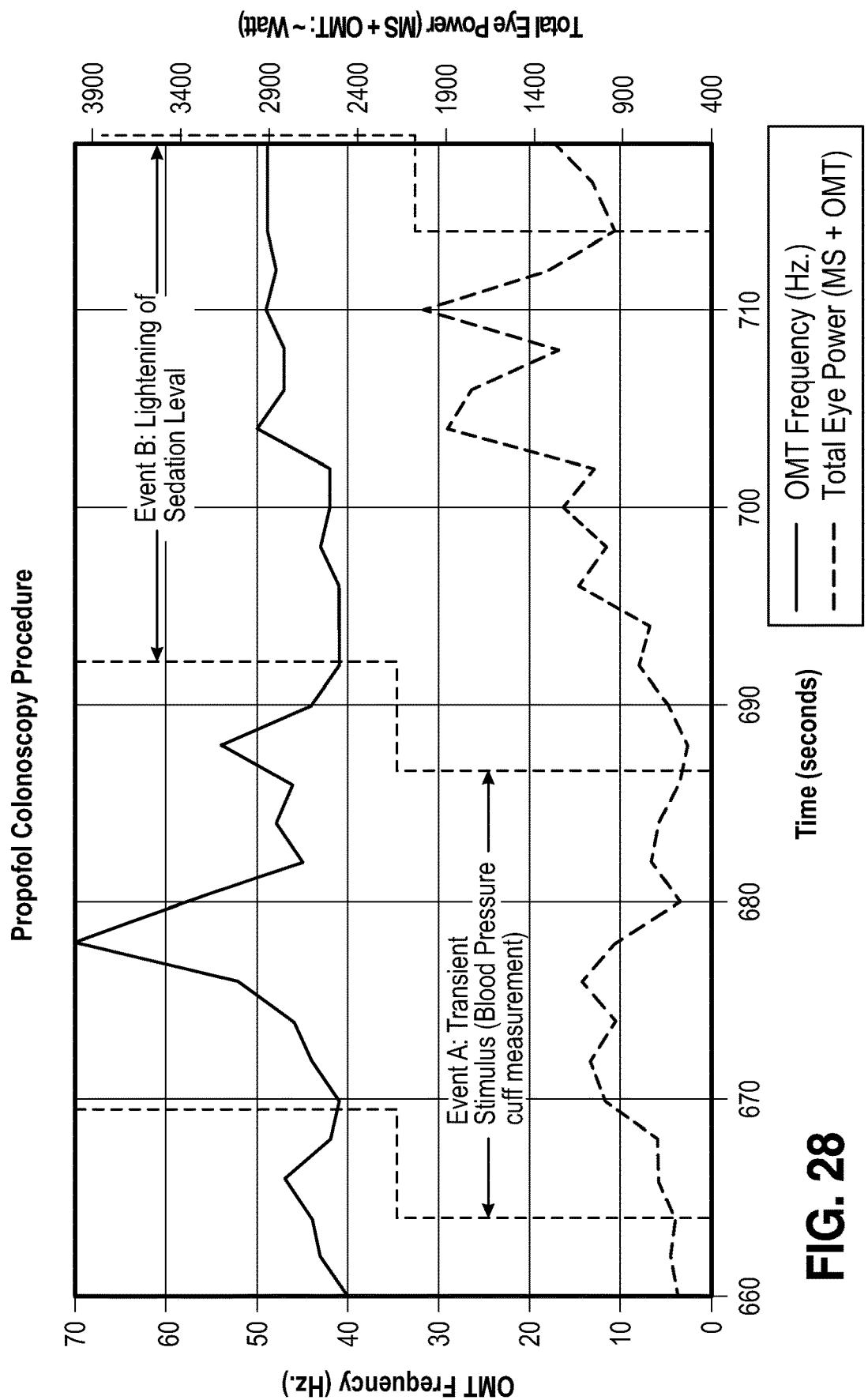
FIG. 28 shows OMT results in the case of an outpatient colonoscopy diagnostic procedure.

In yet another example, as can be seen in FIG. 28, the effectiveness of the use of combination of the reactivity and OMT vs using reactivity and OMT independently are illustrated in the case of an outpatient colonoscopy diagnostic procedure. The embodiments of the invention provide a superior means for adjusting medications. A time period of approximately one minute is illustrated, with the left axis charting OMT peak count frequency as derived and generated with the use of the FAP and methods and the right axis the total eye power as derived and generated with the use of the APC and methods described previously. The ED and EV were used to identify two separate subsequent clinical events as demarked by event A followed by event B. Event A is the resulting reaction of the brainstem to a stimulus applied by the clinician, which was the application of a pressure cuff used to measure blood pressure. Simultaneous review of event A using a comparator shows that over a period of approximately 25 seconds both the OMT frequency value and the Eye power value were relatively steady and low, sharply increased in response to the stimulus and then rapidly fell back to the same values as they were previously. In this case the compared combined data value set comprising values derived from the OMT component and from the MS component considered together in time are compared against a known reference to determine an instruction. In this case when both values rise and fall as described in harmony it is shown statistically to be associated with an external transient stimulus and that no changes to the drug level are required as a result. Up down and back to the same went the values. It should be noted that time synchronization is important and can mean phase retarded, advanced, proportional between before and after etc. or any number of more complicated time based relationships. So long as the multiple data parameters derived from the multiple fixational eye movement components are of a known relationship in time, it is consistent with the present invention.

Turning now the second event depicted in FIG. 28, event B, a true lightening or "wearing off" of the propofol plasma level is occurring. Again through a similar use of the eye sensor processor and routines a comparable constituted combined data set is derived generated and compared. However in this case the pattern recognized by the event SDI is quite different. First the OMT frequency does not return to its previous level, rather notably it is elevated by 10 counts. Secondly, the peak OMT values are not as high, which suggests a more subtle change in frequency associated with a change in brainstem attenuation rather than the pronounced peaks presented in event A. A third characteristic of the pattern is that the Eye power values achieved are higher and more sustained than those of event A. In other words, the total reactivity energy of event B is several fold that of event A. Taken together this combined data pattern including derived values of multiple fixational eye movement components compared in time provide quite different results than the pattern of event A and from the conclusions suggested by the evaluation of either parameter alone. In this case the anesthesiologist administered an additional bolus of propofol just after event B and the signal patterns returned to target levels. It can now be seen that this invention has predictive utility superior to that of the trained professional attending this case, or at least confirmatory utility which is also of tremendous benefit. To review the individual traces shown during event B, the reactivity information as measured by total eye power and energy for sure are larger, but the event appears to return largely to within a few percent of previous values. As such the clinician or operating system is left wondering whether or not to increase medication unnecessarily. Similarly while the OMT value does achieve a new sustained level above that prior to the event, it is level, rather than continuing to climb, again leaving doubt to the operator or system as to what drug administration strategy to follow. Taken together the two parameters increase the confidence of conclusion. This demonstrated result is proven in the statistical analysis of the colonoscopy example where a controlled study was conducted across multiple patients.

It should be noted that propofol used in the colonoscopy case just described is known to be rapid acting and rapid dissipating drug. This is a main driver in its widespread use. It is also dangerous and can lead to immediate catastrophic outcomes. Many other drugs have been measured and can be controlled by the present invention. These include dexmeditomine, sevoflurane, opioids, neuromuscular blockers/paralytics and a range of other agents any of which affect the brainstem of mammals.

Figure 29:
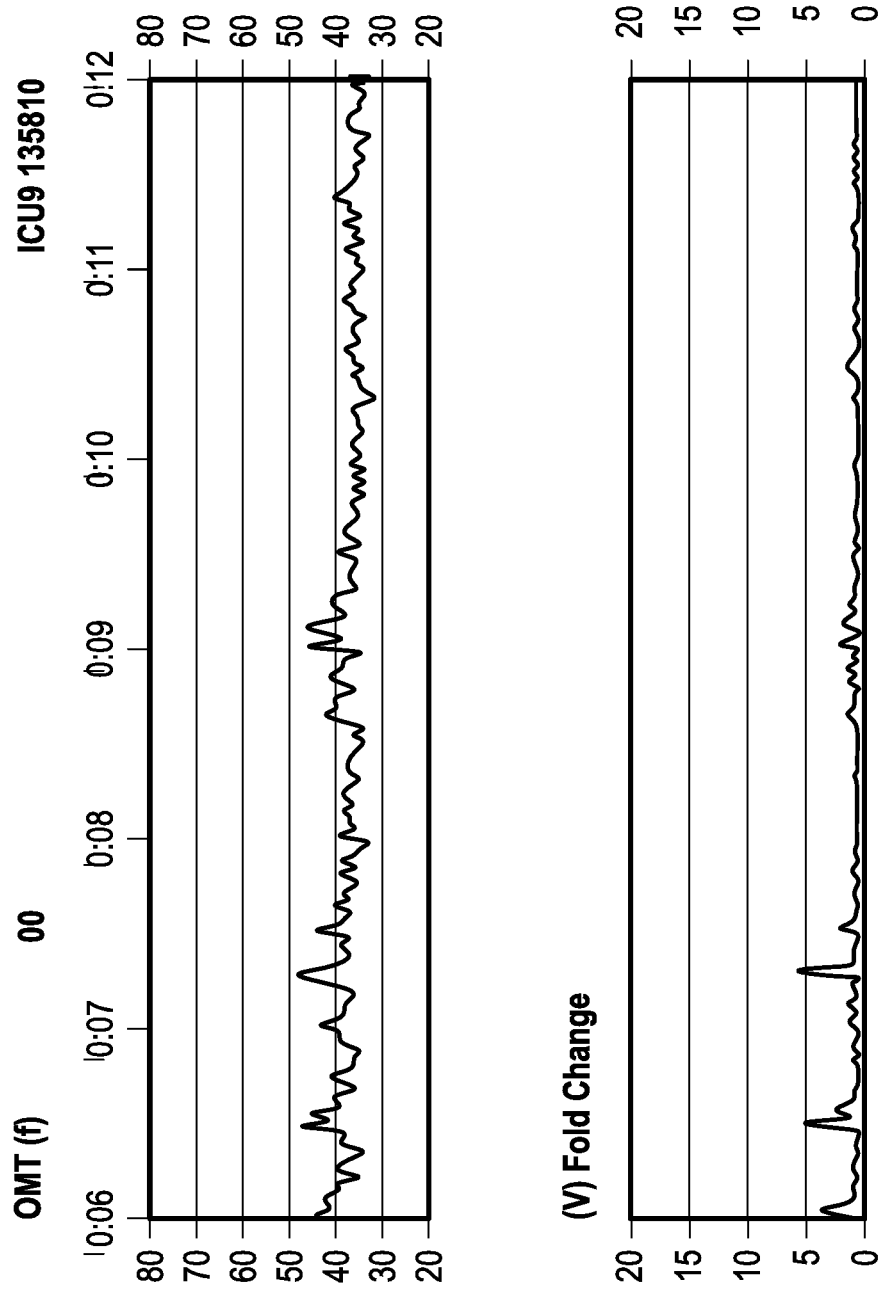
FIG. 29 shows an example of a test showing OMT and a Fold change reactivity.

Turning now to FIG. 29, there is shown one embodiment of a display consistent with the present invention that receives information from the eye sensor processor 9 and routines 114 and displays the information thus making the information accessible to a clinician. The display 9 provides for the real time continuous display of one or more combined parameters derived from fixational eye movement components. The horizontal scale represents clock time or any other measure of time or time-based units. Each of the axes are time-synchronized so as to maintain a relationship between the two in normal operating mode. The horizontal scale is typically set to a default of 20 minutes and displays the most recent 20 minutes of continuously charted data. The duration scale can be varied to show shorter or longer periods or to zoom in on a particular event or time point. The current time period and the current value being recorded and displayed is at the far right most portion of each graph area, and the signal shifts leftward as each 2 second analysis window and recording elapses, as such the displayed trace appears to be moving across the screen from right to left. At the time where the leftmost data point is superseded by the next current new value, the oldest data point drops off the screen out of view.

In an embodiment the upper chart area displays the OMT frequency in units of hertz on the vertical left axis. Proximate to the upper graph area and of a large size to be readable from a 15-20 foot distance is contained a numerical display of the current frequency value being recorded. The frequency value can be the instantaneous value, a 2-second average or a longer average which allows a flexible approach to optimize between real-time precision and stability of the displayed figure. The frequency value in the display box proximate to the upper chart area can also flash, turn to an alternate color or otherwise alert the user in the case that the system detects data portions which are outside of preset values or exceeds filtering conditions.

The lower chart displays a continuously calculated total eye power, calculated using embodiments previously described. The vertical axis of the lower chart depicts the same units of total eye power as was described in FIG. 28 and are measured in units proportional to watts in an embodiment. Proximate to the upper graph area and of a large size to be readable from a 15-20 foot distance is contained a numerical display of the current frequency value being recorded. The frequency value can be the instantaneous value. Proximate to the upper graph area and of a large size to be readable from a 15-20 foot distance is contained a numerical display of the energy change of the most recent event identified by the event detector. In an embodiment, the energy change value can be calculated and displayed in units of fold change. Fold change is similar to the reactivity energy of the event, and is calculated in the same manner. The total energy of the event is computed and the difference in the energy of the event less the energy in the previous most segment is computed and divided by the energy of the previous most segment. In effect to provide the multiple or multi-fold change in energy of the event compared to baseline normal. The value is normalized by dividing by the baseline non-reactive period in order to account for variations between patients and amplitude variations associated with differing levels of sedation and the like.

In another embodiment, the display presents a single continuous live parameter received from the processor 9 and routines 114, but a combined derived computed value derived from the OMT component and the microsaccadic component. The fixational eye movement sedation index is consistent with this embodiment and invention. The numerical display box proximate and large to be seen as described above displays the current value related to the most recent event. The screen is divided into three generally equal portions the uppermost corresponding to light sedation, the middle portion to moderate sedation and the lower portion corresponding to deep sedation. As the sedation index value shifts with clinical circumstance the corresponding portion of the screen is activated in a manner as to illustrate the patient's general state in one of the three zones; light, moderate or deep, and shifts accordingly upon transition there between.

Several other conditions that can be diagnosed or managed in a superior manner over current standards and more effectively than by the use of conventional eye movement sensing techniques will now be disclosed. There are now known derived and generated patterns derived from the frequency, speed, amplitude, power peak velocity, average values, rise times, slopes, fitted curves, ratios, fourier and spectral analyses and the like combinations that indicate statistically significant results. The definitive mark of loss of consciousness, for example is marked by a rapid drop in dominant high frequency peak count followed thereafter by approximately few seconds a rapid exponential or logarithmic decay in the amplitude of the MS component. Regain of consciousness tends to follow a mirrored pattern, but in a nearly square wave fashion, where a preceding strong rise in OMT frequency is followed by a dramatic increase of MS amplitudes.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

It should also be noted that elements of embodiments may be described in reference to the description of a particular embodiment; however it is disclosed that elements of disclosed embodiments can be switched with corresponding elements of embodiments with the same name and/or number of other disclosed embodiments. For example, it is hereby disclosed the identified as 16 the sensor identified as 166, and the sensor identified as 142 are interchangeable with each other in any embodiment where a sensor is disclosed.

Depending on the embodiment, certain steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps. It should also be noted that elements with the use of the terms "upper", "top", "lower", and "bottom" are not to be held as an indication of position; the terms were just employed in the element names for ease of description. For example, an upper element could be located below a lower element.

What is claimed is:

1. A method of measuring fixational eye movements, the method comprising:
    providing a sensor having first and second opposing sides, wherein the sensor is configured to conform to a shape of an eye;
    applying the sensor to an eyelid, with the first side of the sensor disposed adjacent the eyelid and having a curved configuration;
    creating output signals, wherein the creating the output signals comprises the sensor producing a voltage in response to the fixational eye movements, at least one of the output signals represents the fixational eye movements obtained while the eye is open;
    obtaining a combined data set from a frequency component and an amplitude component, wherein the frequency component comprises an ocular microtremor (OMT) frequency of an OMT component, and the amplitude component comprises a microsaccades (MS) amplitude of an MS component, the OMT component and the MS component obtained from said output signals;
    wherein the combined data set comprises the frequency component, the amplitude component, and a time relationship therebetween.

2. The method of claim 1, wherein measuring the fixational eye movements includes measuring brain stem activity.

3. The method of claim 1, wherein measuring the fixational eye movements includes measuring characteristics of sleep.

4. The method of claim 1, wherein measuring the fixational eye movements includes measuring sedation level.

5. The method of claim 1, further comprising isolating the frequency component and the amplitude component from the output signals prior to the obtaining step.

6. The method of claim 5, further comprising amplifying the output signals to render amplified output signals, and wherein the isolating the frequency component and the amplitude component comprises processing the amplified output signals.

7. The method of claim 5, wherein the isolating the frequency component and the amplitude component comprises:
    processing the output signals; wherein the processing the output signals comprises:
    determining a value of the OMT frequency, and determining a value of the MS amplitude, a value of a combined OMT MS amplitude, a value of MS power, a value of MS reactivity, or a combination thereof.

8. The method of claim 5, wherein at least one of the output signals represents the fixational eye movements obtained during an event including a body response, wherein the body response comprises a response to an exogenous stimulus or an arousal event.

9. The method of claim 5, wherein the combined data set further comprises an OMT amplitude, an OMT speed, or a combination thereof.

10. The method of claim 5, wherein the combined data set further comprises an MS frequency, an MS speed, or a combination thereof.

11. The method of claim 5, wherein the isolating further comprises isolating an event component representing an effect of the event.

12. The method of claim 11, wherein the event is an open eye event.

13. The method of claim 5, wherein the output signals coincide with one or more eye openings.

14. The method of claim 1, wherein the amplitude component further comprises an OMT amplitude, and the OMT amplitude is obtained from the output signals.

15. The method of claim 1, wherein the measuring the fixational eye movements comprises comparing the combined data set to at least one known reference.

16. The method of claim 15, further comprising communicating an alert or suggested action based upon the comparing the combined data set to the at least one known reference.

17. The method of claim 1, wherein the sensor produces the voltage in response to the fixational eye movements through the eyelid.

18. The method of claim 1, wherein the sensor is a piezoelectric sensor.

19. The method of claim 1, wherein the measuring the fixational eye movements further comprises (1) producing a reference value, wherein the reference value is based on the combined data set, (2) comparing the combined data set comprising values derived from the OMT frequency and the MS amplitude considered together in time against at least one known reference, or (3) a combination thereof.

* * * * *